United States Patent [19]

Mörsdorf et al.

[11] Patent Number: 4,968,683
[45] Date of Patent: Nov. 6, 1990

[54] 6-OXO-PYRIDAZINE DERIVATIVES, A PROCESS FOR THEIR PREPARATION AND MEDICAMENTS CONTAINING THESE COMPOUNDS

[75] Inventors: Peter Mörsdorf, Langenzenn; Rolf Herter, Schwabach; Heidrun Engler, Cadolzburg; Volker Pfahlert, Munich; Reinhold Weidner; Kurt H. Ahrens, both of Nuremberg, all of Fed. Rep. of Germany

[73] Assignee: Heumann Pharma GmbH & Co., Nuremberg, Fed. Rep. of Germany

[21] Appl. No.: 337,938

[22] Filed: Apr. 14, 1989

[30] Foreign Application Priority Data

Apr. 26, 1988 [DE] Fed. Rep. of Germany ....... 3814057

[51] Int. Cl.$^5$ .................... A61K 31/50; C07D 401/14; C07D 403/14
[52] U.S. Cl. .................... 514/252; 540/575; 544/238; 514/218
[58] Field of Search ............... 544/238; 514/252, 218; 540/575

[56] References Cited

U.S. PATENT DOCUMENTS 4,361,563 11/1982 Austel et al. .................. 514/254

FOREIGN PATENT DOCUMENTS 0208518 1/1987 European Pat. Off. .
0252422 1/1988 European Pat. Off. .
0262448 4/1988 European Pat. Off. .
2837161 3/1980 Fed. Rep. of Germany .
87/05016 8/1987 PCT Int'l Appl. .

OTHER PUBLICATIONS

Chem. Abstracts 103:160462a.
J. Med. Chem. 1985, 28, pp. 1414–1422, Durant et al.

Primary Examiner—Cecilia Shen
Attorney, Agent, or Firm—Burns, Doane, Swecker & Mathis

[57] ABSTRACT

New 6-oxo-pyridazine derivatives corresponding to the general formula I

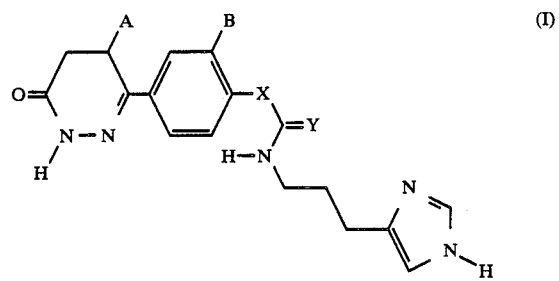

which represent new, positive inotropic compounds having a higher and more selective inotropy-increasing activity are described.

A process of preparation and the medical use of these substances or of a medicament containing these substances are also described.

22 Claims, No Drawings

6-OXO-PYRIDAZINE DERIVATIVES, A PROCESS FOR THEIR PREPARATION AND MEDICAMENTS CONTAINING THESE COMPOUNDS

Digitalis glycosides such as digoxin and digitoxin have now been in use for 200 years in the therapy of cardiac insufficiency. Apart from these, the sympathomimetic drugs are the only therapeutical alternative. Both classes of substances have, however, numerous disadvantages, such as a narrow therapeutic range, tachyphylaxis or lack of availability of a form which can be administered orally.

Moreover, the effectiveness of sympathomimetic drugs is limited for fundamental reasons in certain clinical pictures since, for example, in the case of cardiac infarcts or congestive cardiomyopathy the disease may result in a marked damage of the $\beta$-adrenergic system with a down regulation of the receptors.

Histamine-$H_2$ agonists such as, for example, impromidine (G. J. Durant et al, J. Med. Chem. 28 1414 (1985)) are a new group of cardiotonic substances which represent an interesting alternative for the treatment of the above-mentioned diseases on account of their mechanism of action. It is also known that pyridazinone derivatives such as, for example. Pimobendan (INN) (DE-OS No. 28 37 161, U.S. Pat. No. 4,361,563) and impromidine potentiate themselves in their positive inotropic action. It is an object of the present invention to prepare new positive inotropic compounds which have a higher and more selective inotropy increasing activity.

This invention relates to 6-oxopyridazine derivatives corresponding to the general formula I

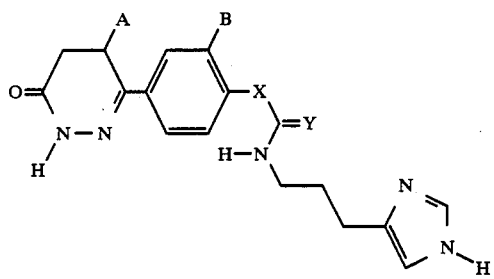

wherein A stands for a hydrogen atom, a $C_1$-$C_3$-alkyl group or a hydroxymethyl group, B stands for a hydrogen atom, a halogen atom, a cyano group or a nitro group, X stands for a group corresponding to one of the following formulae:

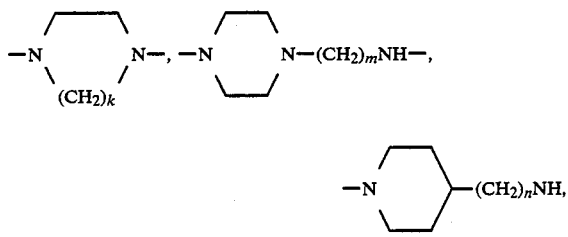

—NH($CH_2$)$_m$NH—, —O($CH_2$)$_n$NH— or —($CH_2$)$_n$NH— wherein k has the value 1, 2 or 3, m has the value 2, 3, 4, 5 or 6 and n has the value 0, 1, 2, 3 or 4 and Y stands for an oxygen atom, a group of the formula =NH, =N—CN,

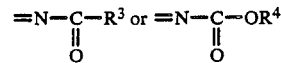

wherein $R^3$ stands for a straight chained or branched $C_1$-$C_6$-alkyl group or for an aryl group optionally substituted with one or more halogen atoms, with $C_1$-$C_3$-alkyl groups or with $C_1$-$C_3$-alkoxy groups and $R^4$ stands for a straight chained or branched $C_1$-$C_4$-alkyl group optionally substituted with one or more halogen atoms, with $C_1$-$C_3$-alkoxy groups or with phenyl groups, and the physiologically acceptable salts thereof.

In the general formula I, A stands for a hydrogen atom, a $C_1$-$C_3$-alkyl group or a hydroxymethyl group.

Examples of the $C_1$-$C_3$-alkyl group are the methyl, ethyl, n-propyl and isopropyl group, the methyl group being preferred. B denotes a hydrogen atom, a halogen atom, for example, a fluorine, chlorine or bromine atom, a cyano group or a nitro group. The preferred halogen atoms are the fluorine and chlorine atom. Compounds in which B stands for a nitro group are particularly preferred.

X stands for a group of one of the following formulae:

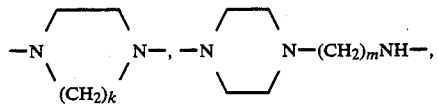

—NH($CH_2$)$_m$NH—, —O($CH_2$)$_n$NH— or —($CH_2$)$_n$NH— in which k has the value 1, 2 or 3, preferably 2. The index m has the value 2, 3, 4, 5 or 6, preferably 2, 3 or 4; n stands for an integer with a value from 0 to 4: Y denotes an oxygen atom or a group of the formula =NH, =N—CN,

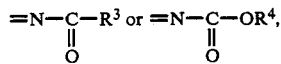

wherein $R^3$ stands for a straight chained or branched $C_1$-$C_6$-alkyl group, preferably a $C_1$-$C_3$-alkyl group, or an aryl group which is optionally mono-, di- or trisubstituted with halogen atoms, with $C_1$-$C_3$-alkyl groups or with $C_1$-$C_3$-alkoxy groups, mono-substitution being preferred, particularly in the p-position. Examples of the $C_1$-$C_6$-alkyl group are the methyl, ethyl, n-propyl, i-propyl, n-butyl and i-butyl group. The aryl group may be, for example, a phenyl or naphthyl group, the phenyl group being preferred. This aryl group may be substituted by halogen atoms and $C_1$-$C_3$-alkyl groups in the same manner as indicated above for groups A and B. Examples for the $C_1$-$C_3$-alkoxy groups include the methoxy, ethoxy and n-propoxy group.

$R^4$ may stand for a straight chained or branched $C_1$-$C_4$-alkyl group optionally mono-, di- or trisubstituted with halogen atoms, for example fluorine, chlorine or bromine atoms, with $C_1-C_3$-alkoxy groups, for example methoxy or ethoxy groups, or with phenyl groups, mono-substitution being preferred, especially at the terminal carbon atom. Y preferably stands for =NH or

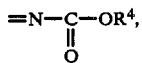

=NH being particularly preferred.

A preferred group of compounds according to the present invention is characterized in that in the general formula I, A stands for a hydrogen atom, a $C_1-C_3$-alkyl group, in particular a methyl group, or a hydroxymethyl group, B stands for a hydrogen atom, a halogen atom, a cyano group or a nitro group, the nitro group being preferred, X stands for a group of the formula

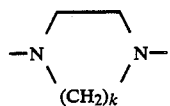

wherein k has the value 1, 2 or 3, preferably the value 2, and Y stands for an oxygen atom or in particular the group =NH.

Another preferred group of compounds according to the invention is characterized in that in the general formula I, A stands for a hydrogen atom, a $C_1-C_3$-alkyl group, preferably a methyl group, or a hydroxymethyl group, B stands for a hydrogen atom, a halogen atom, a cyano group or a nitro group. X stands for a group of the formula

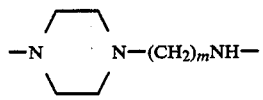

wherein m has the value 2, 3, 4, 5 or 6, and Y stands for an oxygen atom or the group =NH.

Another preferred group of compounds according to the present invention is characterized in that in the general formula I, A stands for a hydrogen atom, a $C_1-C_3$-alkyl group, preferably a methyl group, or a hydroxymethyl group, and B stands for a hydrogen atom, a halogen atom, a cyano group or a nitro group, X stands for a group of the formula

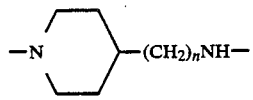

wherein n has the value 0, 1, 2, 3 or 4, and Y stands for an oxygen atom or the group =NH.

One preferred group of compounds according to the invention is characterized in that in the general formula I, A stands for a hydrogen atoms, a $C_1-C_3$-alkyl group, in particular a methyl group, or a hydroxymethyl group, B stands for a hydrogen atom, a halogen atom, a cyano group or a nitro group, X stands for a group of the formula —NH$(CH_2)_m$NH— wherein m has the value 2, 3, 4, 5 to 6, and Y stands for an oxygen atom or the group =NH.

Lastly, another preferred group of compounds according to the present invention is characterized in that in the general formula I, A stands for a hydrogen atom, a $C_1-C_3$-alkyl group or a hydroxymethyl group and B stands for a hydrogen atom, a halogen atom, a cyano group or a nitro group, X stands for a group corresponding to one of the following formulae

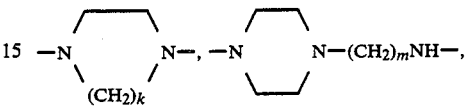

—NH$(CH_2)_m$NH—, —O$(CH_2)_n$NH— or —$(CH_2)_m$NH—, wherein k has the value 1, 2 or 3, m has the value 2, 3, 4, 5 or 6 and n has the value 0, 1, 2, 3 or 4, and Y stands for a group of the formula

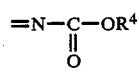

wherein $R^4$ stands for a straight chained or branched $C_1-C_4$-alkyl group optionally substituted with one or more halogen atoms, $C_1-C_3$-alkoxy groups or phenyl rings. The methyl, ethyl and tert.-butyl group are particularly preferred as groups denoted by $R^4$.

The following individual compounds are preferred:
6-[4-[4-[3-(1H-Imidazol-4-yl)propylamino-iminomethylene]piperazin-1-yl]-3-nitro-phenyl]-4,5-dihydro-5-methyl-3(2H)pyridazinone
$N^1$-[3-(1H-Imidazol-4-yl)propyl]-$N^3$-[3-[4-[4-(4-methyl-6-oxo-1,4,5,6-tetrahydropyridazine-3-yl)-2-nitrophenyl]piperazin-1-yl]propyl]-guanidine
$N^1$-[3-(1H-Imidazol-4-yl)propyl]-$N^3$-[2-[4-[4-(4-methyl-6-oxo-1,4,5,6-tetrahydropyridazin-3-yl)-2-nitroanilino]-ethyl]guanidine.

The compounds according to the invention may be prepared by several processes.

One process, which is suitable for the preparation of compounds of the general formula I in which A, B and X have the meanings indicated above and Y stands for one of the groups =NH, =N—CN,

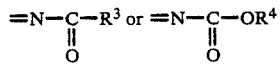

wherein $R^3$ and $R^4$ have the meanings defined above, is characterized in that a compound corresponding to the general formula II

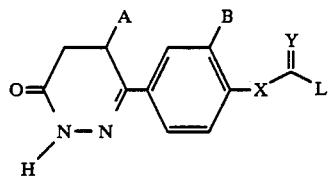

wherein A, B, X and Y have the meanings defined above and L stands for a $C_1$-$C_4$-alkylthio, a phenylthio, a $C_1$-$C_4$-alkoxy or a phenoxy group is reacted with a compound corresponding to formula III

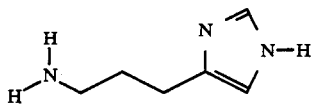

to form a compound corresponding to the general formula I.

On the other hand, compounds according to the invention corresponding to the general formula I in which A, B and X have the meanings defined above and Y stands for one of the groups =NH, =N—CN,

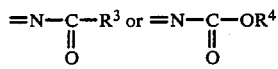

wherein $R^3$ and $R^4$ have the meanings indicated above may be prepared by reacting a compound corresponding to the general formula IV

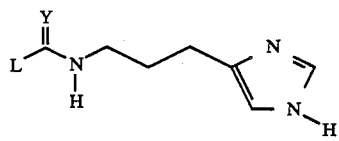

wherein Y and L have the meanings indicated above with a compound corresponding to the general formula V

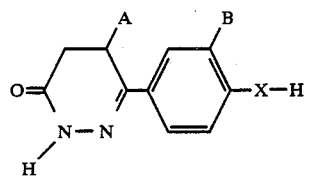

wherein A, B and X have the meanings defined above.

In both variations of the process, the leaving group L in the compounds of formulae II and IV is preferably the $C_1$-$C_4$-alkylthio groups, in particular the methylthio group, and the phenoxy group. Compounds corresponding to the general formulae II and IV are preferably put into the process in a ratio of from 1:1 to 0.8:1, most preferably in equimolar quantities, based on the compounds corresponding to the general formulae III and V. The reactions are carried out in a polar solvent such as acetonitrile, pyridine, dimethylformamide or alcohol, preferably a secondary or a tertiary alcohol such as, for example, isopropanol or mixtures thereof and at temperatures ranging from 20° C. to the reflux temperature of the solvent used.

Compounds corresponding to the general formula I in which A, B and X have the meanings defined above and Y stands for the group NH may also be prepared by hydrolysing a compound corresponding to the general formula Ia

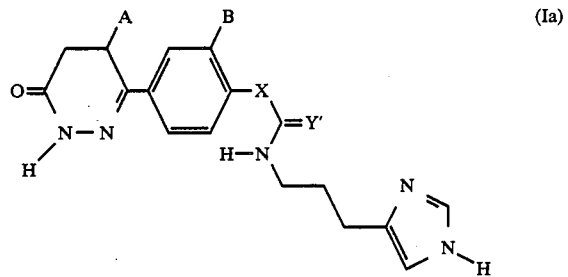

wherein A, B and X have the meanings indicated above and Y' stands for one of the groups =N—CN,

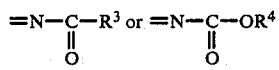

in which $R^3$ and $R^4$ have the meanings defined above by acid or basic hydrolysis to form a compound corresponding to the general formula I in which Y stands for the group =NH, and optionally decarboxylating. Acid hydrolysis is carried out, for example, in an aqueous mineral acid such as hydrochloric or hydrobromic acid or sulphuric acid and at temperatures of from 20° to 100° C.; preferably from 30° to 80° C. It may, however, be preferable, for example when Y' stands for the group

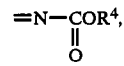

to employ non-aqueous reaction conditions. Such milder methods are, for example, solvolysis with trifluoroacetic acid in a chlorinated hydrocarbon such as dichloromethane or chloroform, or the reaction with hydrobromic acid in glacial acetic acid.

Basic hydrolysis is carried out in a diluted solution of alkali metal or alkaline earth metal carbonates or alkali metal or alkaline earth metal hydroxides in water, lower alcohols or mixtures of the two and at temperatures from room temperature to the reflux temperature of the solvent used.

Compounds according to the invention corresponding to the general formula I in which A, B and X have the meanings indicated above and Y stands for an oxygen atom may be prepared by reacting a compound corresponding to the general formula VI

wherein Z stands for a halogen atom or the group of an azole or benzazole which has at least two nitrogen atoms in the 5-membered ring and is attached to a nitrogen atom, successively with a compound corresponding to the general formula V

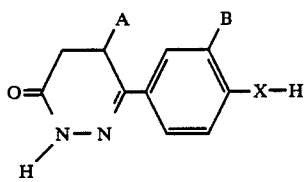 (V)

wherein A, B and X have the meanings defined above and then with a compound corresponding to formula III

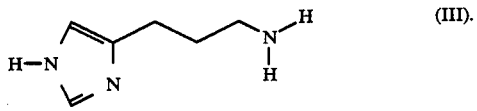 (III).

The reactions of the compound corresponding to the general formula VI with the compounds of formulae V and III may be carried out in any sequence but it is preferable first to react the compound of formula VI with a compound of formula V and then with the compound of formula III. The reactions are normally carried out as a one-pot reaction, i.e. the intermediate stages are neither isolated nor purified.

Examples of the azoles and benzazoles defined by Z include the imidazole, the 1,2,4-triazole, the tetrazole, the benzimidazole or, the benzotriazole ring. N,N'-Carbonyldiimidazole is a preferred compound corresponding to the general formula VI. The reactions are carried out in an inert solvent, for example a halogenated hydrocarbon such as dichloroethane, an ether, for example tetrahydrofuran, or polar solvents such as acetonitrile or dimethylformamide. The reaction temperatures may be in the range of from $-20°$ C. to the boiling point of the solvent used. If Z in the general formula VI stands for a halogen atom, it is advisable to add an acid acceptor, for example a tertiary amine such as triethylamine or pyridine.

The compounds obtained by the different variations of the process are isolated and purified in the usual manner, for example by recrystallisation, chromatographic methods, etc. The compounds obtained from the individual variations of the process may, if desired, be converted into physiologically acceptable salts thereof. These salts may be formed, for example, with mineral acids such as hydrochloric, hydrobromic or hydriodic acid, phosphoric acid, metaphosphoric acid, nitric acid or sulphuric acid or with organic acids such as formic acid, acetic acid, propionic acid, phenylacetic acid, tartaric acid, citric acid, fumaric acid, methanesulphonic acid, embonic acid, etc.

The compounds according to the invention corresponding to the general formula I may be present in several tautomeric forms and in several stereoisomeric forms. The invention therefore covers not only the salts and hydrates of the above-described compounds of the general formula I but also the tautomeric and stereoisomeric forms thereof.

The compounds according to the invention may be formulated in any desired manner for administration. The invention therefore also covers medicaments containing at least one compound according to the invention for use in human or veterinary medicine. Such medicaments may be prepared by conventional methods, using one or more pharmaceutically acceptable carriers or diluents.

The compounds according to the invention may therefore be formulated for oral, buccal, topical, parenteral or rectal administration.

For oral administration, the medicament may be in the form of, for example, tablets, capsules, powders, solutions, syrups or suspensions prepared by conventional methods, using acceptable diluents.

For buccal administration, the medicament may take the form of tablets or sachets formulated in conventional manner.

The compounds according to the invention may be formulated for parenteral administration by bolus injection or continuous infusion. Formulations for injection may be made up into ampoules of unit doses or they may be prepared in multiple dose containers with added preservative. The medicaments may assume forms such as suspensions, solutions or emulsions in oily or aqueous carriers and they may contain formulating auxiliaries such as suspending, stabilizing and/or dispersing agents.

Alternatively, the active ingredient may be provided in powder form to be reconstituted before use with a suitable carrier such as sterile, pyrogen-free water.

The compounds according to the invention may also be formulated for rectal preparations such as suppositories and retention enemas containing, for example, conventional suppository excipients such as cocoa butter or other glycerides.

For topical application, the compounds according to the invention may be formulated in conventional manner as ointments, creams, gels, lotions, powders or sprays.

For oral administration, a suitable daily dose of compounds according to the invention is 1 to 4 doses up to a total amount of 5 mg to 1 g per day, depending on the patient's condition. It may be necessary in individual cases to deviate from the quantities indicated, depending on the individual response to the active ingredient or the nature of its formulation and the time or time interval at which the medicament is administered. Thus, for example, there are cases in which less than the minimum quantity indicated above may be sufficient whereas in other cases it may be necessary to exceed the upper limit indicated above.

The 6-oxo-pyridazine derivatives according to the invention corresponding to the general formula I show pronounced cardiovascular in particular cardiotonic actions and are therefore suitable for the treatment and prevention of diseases of the heart and circulation.

Thus they show an excellent positive inotropic action in a series of in vitro and in vivo standard models, e.g. in the isolated, perfused Langendorff heart and in narcotised guinea-pigs after intravenous application.

(1.) Positive inotropic action on isolated, perfused Langendorff heart (guinea-pig)
  (a) Method
  To determine the haemodynamic effects of the compounds according to the invention on isolated, perfused guinea-pig hearts, the arrangement of Langendorff was modified according to P. R. Beckett (J. Pharm. Pharmacol 22, 818 (1970)) and R. M. Abel and R. L. Reis (Circ. Res. 27, 961 (1970)). The spontaneously beating guinea-pig hearts are catheterised in the left ventricle and perfused with solutions of the test substances in physiological saline solution/ethanol (9:1) at concentrations of from $10^{-4}$ to $10^{-8}$ mol/l at a constant perfusion pressure of 60 mm Hg.

(b) Measured results

| Example No. | Concentration (mol/l) | Increase in contractility LV dp/dt compared with initial values |
|---|---|---|
| 1 | $10^{-6}$ | +90% |
|   | $10^{-5}$ | +100% |
| 3 | $10^{-6}$ | +50% |
|   | $10^{-5}$ | +100% |
| 5 | $10^{-5}$ | +200% |
| 6 | $10^{-7}$ | +67% |
|   | $10^{-6}$ | +220% |

2. Haemodisation on the narcotised guinea-pig (i.v. Application)

(a) Method

The animals are narcotized with urethane (1.5 g/kg). The trachea is cannulated for volume controlled breathing. The two carotid arteries are then exposed operatively. A Tip catheter (3F) is introduced through the right carotid artery and moved forwards into the left ventricle through the ascending aorta under continuous recording of the pressure. Successful passage through the aortic valves is recognized by the typical left ventricular pressure curve. A thermistor sensor (3F, F. Edwards) is pushed forwards into the aortic arc through the left carotid for thermodilution. The thermistor sensor has a lumen for recording the arterial blood pressure. A catheter is placed in front of the right auricle through the right jugular vein for application of the cold injectate (0.2 ml of 0.9% NaCl, 15° C.). All the substances are dissolved in physiological saline solution and are infused through the left jugular vein (infusion volume 0.02 ml/min): the substances are applied after haemodynamic stabilization and under β blockage (Metoprolol 2 mg/kg i.m.). All circulatory parameters are continuously recorded on a direct recorder. The contractility (dp/dt) is calculated from the volume curve.

(b) Measured values

| Example No. | Dose μg/kg/min | Maximum increase in contractility LD dp/dt |
|---|---|---|
| 1 | 5 | +100% |
| 3 | 10 | +90% |
| 6 | 5 | +200% |

The examples which follow illustrate the invention. The intermediate products were tested routinely for purity by thin layer chromatography, using UV light and spray reactants such as Echtblau salt B/sodium hydroxide solution for proof.

The preparative chromatography was carried out using silica gel (Merck, Art. No. 7734 and 7749). Thin layer chromatography was carried out on silica gel films Polygram SIL G/UV$_{254}$ (Machery-Nagel).

The following abbreviations are used for the eluting agent:

| A | Dichloromethane/methanol | 95:5 |
|---|---|---|
| B | Dichloromethane/methanol/conc. ammonia | 90:7:3 |
| C | Dichloromethane/methanol/conc. ammonia | 85:13:2 |
| D | Ethyl acetate/buffer* | 50:50 |
| E | Ethyl acetate/buffer* | 60:40 |
| F | Ethyl acetate/methanol/conc. ammonia | 80:18:2 |
| G | Ethyl acetate/buffer | 70:30 |
| H | Dichloromethane/methanol | 90:10 |

*Buffer:methanol/conc. ammonia saturated with ammonium chloride 95:5

EXAMPLE 1

$N^1$-[3-(1H-Imidazol-4-yl)propyl]-$N^3$-[2-[4-(4-methyl-6-oxo-1,4,5,6-tetrahydropyridazin-3-yl)-2-nitro-anilino]ethyl]guanidine

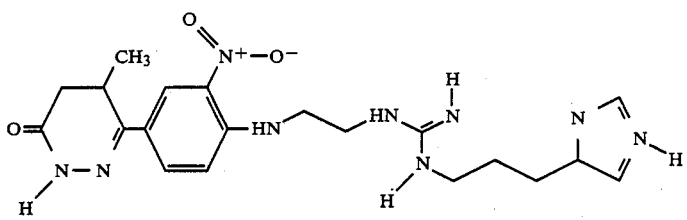

$N^1$-Benzoyl-$N^2$-[2-[4-(4-methyl-6-oxo-1,4,5,6-tetrahydropyridazin-3-yl)-2-nitro-anilino]ethyl]-thiourea 2.8 g (17.1 mmol) of benzoyl isothiocyanate are added to a suspension of 5.0 g (17.1 mmol) of N-[4-(4-methyl-6-oxo-1,4,5,6-tetrahydropyridazin-3-yl)-2-nitro-phenyl]ethylene diamine in 50 ml of acetonitrile and the reaction mixture is stirred at room temperature for one hour. The precipitated solid is separated by suction filtration, washed with acetonitrile and boiled up with 100 ml of ethanol. 6.4 g (82%) of an orange yellow solid, m.p. 177° C., are obtained after cooling and suction filtration.

$C_{21}H_{22}N_6O_4S$ (454.50)

Rf=0.73 (Solvent H)

(b)

N-[2-[4-(4-Methyl-6-oxo-1,4,5,6-tetrahydropyridazin-3-yl)-2-nitro-anilino]ethyl]-thiourea 2.00 g (4.4 mmol) of $N^1$-Benzoyl-$N^2$-[2-[4-(4-methyl-6-oxo-1,4,5,6-tetrahydropyridazin-3-yl)-2-nitro-anilino]ethyl]-thiourea are boiled up with 1.20 g (8.7 mmol) of potassium carbonate in 75 ml of methanol and 15 ml of water for one hour. The precipitated solid is suction filtered and recrystallized from methanol. 1.37 g (89%) of an orange coloured solid melting at 231°-233° C. are obtained.

$C_{14}H_{18}N_6O_3S$ (350.39)

Rf=0.43 (Solvent H)

(c)

N-[2-[4-(4-Methyl-6-oxo-1,4,5,6-tetrahydropyridazin-3-yl)-2-nitro-anilino]ethyl]-S-methyl-isothiuronium iodide 1.35 g (3.85 mmol) of the thiourea from stage (b) and 0.26 ml (4.2 mmol) of methyl iodide are stirred together for 2.5 hours in 20 ml of dimethylformamide at room temperature. The solution is filtered and the filtrate is concentrated by evaporation under vacuum at 70° C.

The residue yields 1.33 g (70%) of orange-coloured crystals, m.p.145°–147° C., after crystallization with 20 ml of ethanol.

$C_{15}H_{21}IN_6O_3S$ (492.33)

Rf=0.18 (Solvent H)

(d)

$N^1$-[3-(1H-Imidazol-4-yl)propyl]-$N^3$-[2-[4-(4-methyl-6-oxo-1,4,5,6-tetrahydropyridazin-3-yl)-2-nitro-anilino]ethyl]-guanidine 1.00 g (2.03 mmol) of N-[2-[4-(4-Methyl-6-oxo-1,4,5,6-tetrahydropyridazin-3-yl)-2-nitro-anilino]ethyl]-S-methylisothiuronium iodide and 0.28 g (2.23 mmol) of 3-(1H-imidazol-4-yl)-propylamine are boiled in 20 ml of pyridine for 3 hours. After cooling, the red solution is concentrated by evaporation under vacuum and the residue is chromatographed on silica gel, using ethyl acetate/methanol/conc. ammonia saturated with ammonium chloride (50:47.5:2.5) as solvent. The main fraction is concentrated by evaporation under vacuum, the residue is taken up with 10 ml of saturated potassium carbonate solution and the aqueous phase is extracted with 3×10 ml of isopropanol. After the organic phases have been dried, filtered and concentrated by evaporation under vacuum, they yield an orange yellow foam which is crystallized with ethanol. 0.40 g (45%) of a solid which does not have a sharp melting point is obtained.

$C_{20}H_{27}N_9O_3$ (441.49)

Rf=0.38 (Solvent D)

| $^1$H-NMR data (DMSO-d$_6$, TMS as internal standard) | $\delta$ = 1.05 | (d) | 3H |
|---|---|---|---|
| | 1.72 | (quin) | 2H |
| | 2.15–2.80 | (m) | 4H |
| | 3.10 | (t) | 2H |
| | 3.2–3.6 | (m) | 5H |
| | 6.75 | (s) | 1H |
| | 7.23 | (d) | 1H |
| | 7.50 | (s) | 1H |
| | 7.95 | (dd) | 1H |
| | 8.38 | (d) | 1H |
| | 8.6 | (broad) | 6H |
| | replaceable by D$_2$O ppm | | |

EXAMPLE 2

6-[4-[4-[3-(1H-Imidazol-4-yl)propylamino-iminomethylene]piperazin-1-yl]phenyl]-4,5-dihydro-5-methyl-3(2H)-pyridazinone

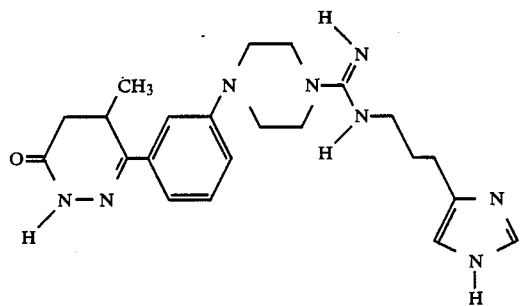

2.00 g (4.2 mmol) of 6-[4-[4-(Methylthio-iminomethylene)piperazin-1-yl]phenyl]-4,5-dihydro-5-methyl-3(2H)-pyridazinone hydriodide and 0.58 g (4.7 mmol) of 3-(1H-imidazol-4-yl)-propylamine are boiled under reflux in 50 ml of acetonitrile for 3 hours. The oil obtained after concentration of the solution by evaporation under vacuum is chormatographed on silica gel, using ethyl acetate/methanol/conc.ammonia saturated with ammonium chloride (70:28.5:1.5) as solvent. The main fraction is concentrated by evaporation under vacuum and the residue is taken up with 10 ml of saturated potassium carbonate solution and extracted with 2×10 ml of isopropanol. After drying and concentration of the organic phase by evaporation, an amorphous solid is left behind which crystallizes as an isopropanolate when titrated with a small quantity of isopropanol.

$C_{22}H_{30}N_8O_x \cdot C_3H_8O$ (482.61)

Rf=0.55 (Solvent D)

| $^1$H-NMR data (DMSO-D$_6$, TMS as internal standard) | $\delta$ = 1.02–1.14 | (2d) | 9H |
|---|---|---|---|
| | 1.76 | (quin) | 2H |
| | 2.4–3.9 | (m) | 16H |
| | 6.70 | (s) | 1H |
| | 6.98 | (d) | 2H |
| | 7.49 | (s) | 1H |
| | 7.63 | (d) | 2H |
| | 10.85 | (broad) | 1H |
| | replaceable by D$_2$O | | |

EXAMPLE 3

6-[4-[4-[3-(1H-Imidazol-4-yl)propylamino-iminomethylene]piperazin-1-yl]-3-nitro-phenyl]-4,5-dihydro-5-methyl-3(2H)-pyridazinone

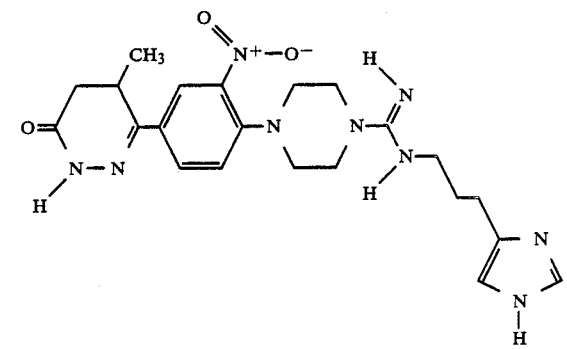

(a)

6-[4-[4-(Benzoylamino-thiocarbonyl)piperazin-1-yl]-3-nitro-phenyl]-4,5-dihydro-5-methyl-3(2H)-pyridazinone 27.0 g (0.165 mol) of benzoyl isothiocyanate are added at room temperature to 52.4 g (0.165 mol) of 6-[4-(1-piperazinyl)-3-nitro-phenyl]-4,5-dihydro-5-methyl-3(2H)-pyridazinone in 1200 ml of 1,4-dioxane. The reaction mixture is stirred at room temperature for 2 hours and then concentrated to 700 ml under vacuum and left to crystallize. 76 05 g (96% of theoretical) of orange-yellow crystals melting at 174.5°–177° C. are obtained after suction filtration.

$C_{23}H_{24}N_6O_4S$ (480.55)

Rf=0.58 (Solvent B)

(b)

6-[4-[4-(Amino-thiocarbonyl)-piperazin-1-yl]-3-nitro-phenyl]-4,5-dihydro-5-methyl-3(2H)-pyridazinone 66.6 g (0.139 mol) of the compound synthesized as described under (a) are boiled under reflux in 1200 ml of methanol and 150 ml of water in the presence of 21.6 g (0.156 mol) of potassium carbonate.

500 ml of methanol are distilled off after 12 hours and the reaction mixture is cooled to room temperature. 35.5 g (68% of theoretical) of the product crystallize as orange-red crystals melting at 238.0°–239.5° C.

$C_{16}H_{20}N_6O_3S$ (376.44)

Rf=0.62 (Solvent F)

(c)
6-[4-[4-(Methylthio-iminomethylene)piperazin-1-yl]-3-nitro-phenyl]-4,5-dihydro-5-methyl-3(2H)-pyridazinone hydriodide 8.0 ml (0.127 mol) of Methyl iodide in 20 ml of DMF are added dropwise to a suspension of 42.4 g (0.113 mol) of the compound obtained as described under (b) in 300 ml of dimethylformamide.

The clear solution is then stirred for 4 hours at room temperature.

After removal of the dimethylformamide by distillation in a medium high vacuum, a red oil is left behind, from which 52.7 g (90% of theoretical) of an orange-yellow solid melting in the range of 179.8°–181.3° C. crystallize after the addition of 200 ml of ethanol.

$C_{17}H_{23}IN_6O_3S$ (518.37)

Rf=0.58 (Solvent F)

(d)
6-[4-[4-[3-(1H-Imidazol-4-yl)propylamino-iminomethylene]
piperazin-1-yl]-3-nitro-phenyl]-4,5-dihydro-5-methyl-(2H)-pyridazinone 2.07 g (4 mmol) of the compound obtained as described under (c) and 0.50 g (4 mmol) of 3-(1H-Imidazol-4-yl)propylamine are stirred together in 10 ml of pyridine for 15 hours at room temperature.

10 ml of a 10% aqueous potassium carbonate solution are added and the reaction mixture is extracted with a total of 50 ml of chloroform/methanol (80/20 v/v). After removal of the organic solvents by evaporation under vacuum, 20 ml of ethanol are added to the residue. 1.4 g (75% of theoretical) of the title compound crystallize as a yellow powder melting at 225°–226° C.

$C_{22}H_{29}N_2O_3$ (467.54)

RF=0.38 (Solvent D)

| 1H-NMR data (DMSO-d6, TMS as internal standard) | δ = 1.06 | (d) | 3H |
|---|---|---|---|
| | 1.83 | (q) | 2H |
| | 2.25 | (d) | 1H |
| | 2.56 | (t) | 2H |
| | 2.71 | (dd) | 1H |
| | 3.24 | (m) | 6H |
| | 3.42 | (m) | 1H |
| | 3.58 | (m) | 4H |
| | 6.63 | (s) | 1H |
| | 7.37 | (d) | 1H |
| | 7.59 | (s) | 1H |
| | 7.4–8.4 | (broad) | 2H, replaceable by D2O, |
| | 7.99 | (dd) | 1H |
| | 8.21 | (d) | 1H |
| | 11.05 | (s) | 1H |
| | 11.8 | (broad) | 1H, replaceable by D2O, ppm |

EXAMPLE 4

$N^1$-[3-(1H-Imidazol-4-yl)propyl]-$N^3$-[4-(4-methyl-6-oxo-4,5,6-tetrahydro-pyridazin-3-yl)-2-nitro-phenyl]-guanidine

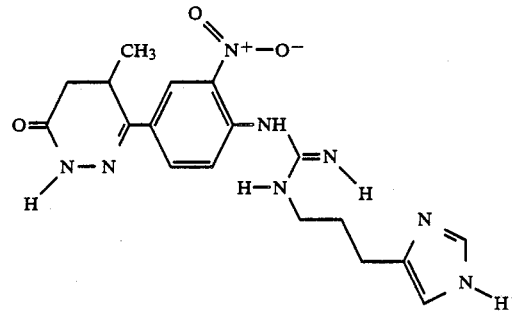

(a)
$N^1$-Benzoyl-$N^2$-[4-(4-methyl-6-oxo-1,4,5,6-tetrahydropyridazin-3-yl)-2-nitro-phenyl]-thiourea 10.0 g (40.3 mmol) of 6-(4-Amino-3-nitro-phenyl)-4,5-dihydro-5-methyl-3(2H)-pyridazinone are boiled under reflux with 7.2 g (44.3 mmol) of benzoylisothiocyanate in 300 ml of dioxane for 10 hours. The solvent is drawn off under vacuum and the residue is boiled under reflux for 30 minutes in 200 ml of ethanol. After cooling to room temperature and suction filtration, 14.0 g (84% of theoretical) of an orange-yellow powder melting at 204.9°–205.4° C. are obtained.

$C_{19}H_{17}N_5O_4S$ (411.44)

Rf=0.69 (Solvent A)

(b)
6-(4-Cyanamino-3-nitro-phenyl)-4,5-dihydro-5-methyl-3(2H)-pyridazinone 10.0 g (24.3 mmol) of the compound obtained as described under (a) are boiled under reflux for 2 hours with 3.4 g (24.3 mmol) of potassium carbonate in 200 ml of methanol and 35 ml of water.

The dark red solution is cooled and the precipitated solid is separated by suction filtration and washed with a small quantity of methanol. The filter cake is dissolved in 70 ml of hot water and acidified to pH 5 with glacial acetic acid.

When suction filtration is repeated in the cold, 3.4 g (51% of theoretical) of pale yellow crystals melting at 234.5°–235.9° C. are obtained.

$C_{12}H_{11}N_5O_3$ (273.29)

Rf=0.41 (Solvent A)

(c) $N^1$-[3 (1H-Imidazol-4-yl)propyl]-$N^3$-[4-(4-methyl-6-oxo-1,4,5,6-tetrahydro-pyridazin-3-yl)-2-nitro-phenyl]guanidine 1.0 g of a 33% isopropanolic hydrochloric acid is added to a solution in 40 ml of methoxyethanol of 1.8 g (6.6 mmol) of the solids obtained as described under (b) and 1.2 g (9.9 mol) of 3-(1H-imidazol-4-yl)-propylamine. The reaction mixture is boiled under reflux for 3 hours and cooled and 10 ml of a saturated, aqueous potassium carbonate solution are added, and the product is extracted with tetrahydrofuran.

After removal of the solvent by evaporation at reduced pressure, the residue is chromatographed on silica gel (Solvent E).

The main fractions are concentrated by evaporation, the residue is divided between aqueous potassium carbonate solution and tetrahydrofuran, and the organic phase is concentrated by evaporation.

Treatment of the residue with ethanol yields 1.1 g (42% of the theoretical) of an orange-yellow powder which starts to soften at 155° C. and contains ⅓ of a molar equivalent of ethanol.

$C_{18}H_{22}N_8O_3 \times \frac{1}{3} C_2H_6O$ (413.78)

Rf=0.65 (Solvent D)

| $^1$H-NMR data (DMSO-$d_6$, TMS as internal standard) | $\delta$ = 1.07 | (d) | 3H |
|---|---|---|---|
| | 1.75 | (q) | 2H |
| | 2.23 | (d) | 1H |
| | 2.56 | (m) | 2H |
| | 3.13 | (q) | 2H |
| | 3.43 | (m) | 1H |
| | 5.54 | (s) | 2H, replaceable by D$_2$O, |
| | 6.09 | (t) | 1H, replaceable by D$_2$O, |
| | 6.74 | (s) | 1H |
| | 7.02 | (d) | 1H |
| | 7.49 | (s) | 1H |
| | 7.80 | (dd) | 1H |
| | 8.06 | (d) | 1H |
| | 10.94 | (s) | 1H |
| | 11.79 | (broad) | 1H, replaceable by D$_2$O, ppm |

EXAMPLE 5

6-[4-[4-[3-(1H-Imidazol-4-yl)propylamino-iminomethylene]piperazin-1-yl]-3-nitro-phenyl]-4,5-dihydro-3(2H)-pyridazinone

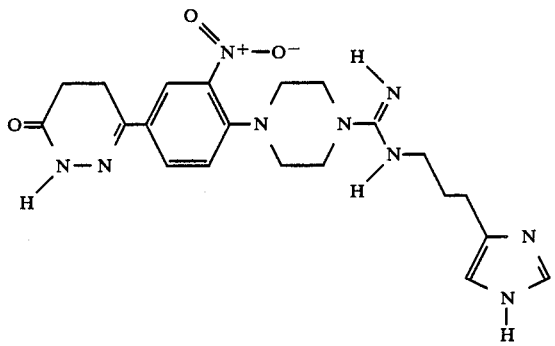

(a)
6-[4-[4-(Benzoylamino-thiocarbonyl)piperazin-1-yl]-3-nitro-phenyl]-4,5-dihydro-3(2H)-pyridazinone A solution of 5.2 g (32 mmol) of benzoyl isothiocyanate in 20 ml of chloroform is added dropwise at room temperature to a suspension of 8.8 g (29 mmol) of 6-[4-(1-piperazinyl)-3-nitro-phenyl]-4,5-dihydro-3(2H)-pyridazinone in 300 ml of chloroform. The reaction mixture is stirred for 2 hours at 30° C. and cooled in an ice bath and the precipitated solid is separated by suction filtration. 12.5 g (93% of theoretical) of orange coloured crystals melting at 140°–141.5° C. remain after drying.

$C_{22}H_{22}N_6O_4S$ (466.52)

Rf=0.72 (Solvent F)

(b) 6-[4-[4-(Amino-thiocarbonyl)piperazin-1 yl]-3-nitrophenyl]-4,5-dihydro-3(2H)-pyridazinone 12.0 g (25.7 mmol) of the benzoyl compound obtained as described under a) are boiled under reflux with 5.4 g (39 mmol) of potassium carbonate in 210 ml of methanol and 35 ml of water. The reaction mixture is left to cool to room temperature after 22 hours and a solid crystallizes.

After separation of the solid by suction filtration and washing with a small quantity of ethanol, 7.19 g (76% of the theoretical) of an orange solid melting at 222.5°–223.8° C. are obtained.

$C_{15}H_{18}N_6O_3S$ (362.41)

Rf=0.51 (Solvent F)

(c)
6-[4-[4-(Methylthio-iminomethylene)piperazin-1-yl]-3-nitro-phenyl]-4,5-dihydro-3(2H)-pyridazinone hydriodide 6.7 g (18.5 mmol) of the thiourea obtained as described under (b) are suspended in 500 ml of CHCl$_3$ and 120 ml of CH$_3$OH and 7.5 ml of methyl iodide are added.

The reaction mixture is boiled under reflux for 5 hours and then left to cool, suction filtered and washed with a small quantity of chloroform.

6.8 g (73% of theoretical) of yellow crystals melting at 209°–212° C. are obtained.

$C_{16}H_{21}IN_6O_3S$ (504.34)

Rf=0.65 (Solvent B)

(d)
6-[4-[4-[3-(1H-Imidazol-4-yl)propylamino-iminomethylene]piperazin-1-yl]-3-nitro-phenyl]-4,5-dihydro-3(2H)-pyridazinone 3.0 g (5.9 mmol) of 6-[4-[4-(Methylthio-iminomethylene)piperazin-1-yl]-3-nitro-phenyl]-4,5-dihydro-3(2H)-pyridazinone are boiled under reflux for 2 hours with 1.1 g (8.9 mmol) of 3-(1H -imidazol-4-yl)-propylamine in 100 ml of acetonitrile.

After the reaction mixture has cooled, 40 ml of a saturated aqueous potassium carbonate solution are added, the organic phase is separated and the aqueous phase is extracted with 50 ml of chloroform/methanol (80/2 v/v). The organic phases are combined and concentrated by evaporation and the residue is chromatographed on silica gel (Solvent F).

The main fractions are combined and concentrated by evaporation. Saturated potassium carbonate solution is added to the residue and the latter is extracted with chloroform/methanol (80/20 v/v). The solvent is concentrated by evaporation under vacuum and the oil remaining behind is crystallized from a small quantity of isopropanol 0.56 g (21% of theoretical) of an orange-red powder melting at 204.8°–205.4° C. is obtained.

$C_{21}H_{27}N_9O_3$ (453.51)

Rf=0.40 (Solvent D)

| $^1$H-NMR data (DMSO-$d_6$, TMS as internal standard) | $\delta$ = 1.73 | (m) | 2H |
|---|---|---|---|
| | 2.4–2.6 | (m) | 6H |
| | 2.9 | (m) | 2H |
| | 3.0 | (m) | 4H |
| | 3.3 | (m) | 4H |
| | 3.0–3.8 | (broad) | 3H, replaceable by D$_2$O, |
| | 6.69 | (s) | 1H |
| | 7.34 | (d) | 1H |
| | 7.48 | (s) | 1H |
| | 7.92 | (dd) | 1H |

| 8.13 | (s) | 1H |
| 10.95 | (broad) | 1H, replaceable by D$_2$O, ppm |

EXAMPLE 6

N$^1$-[3-(1H-Imidazol-4-yl)propyl]-N$^3$-[3-[4-[4-(4-methyl-6-oxo-1,4,5,6-tetrahydro-pyridazin-3-yl)-2-nitro-phenyl]piperazin-1-yl]propyl]-guanidine

(a)
6-[3-Nitro-4-[4-(3-phthalimido-propyl)piperazin-1-yl]phenyl]-5-methyl-4,5-dihydro-3(2H)-pyridazinone 31.63 g (0.1 mol) of 6-[4-(1-Piperazinyl)-3-nitro-phenyl]-4,5-dihydro-5-methyl-3(2H)-pyridazinone and 26.81 g (0.1 mol) of 1-(3-bromopropyl)-phthalimide are stirred together in 500 ml of DMF in the presence of 13.8 g (0.1 mol) of potassium carbonate and 0.4 g of potassium iodide at 100° C. for 24 hours.

The reaction mixture is left to cool to 40° C. and then poured out on 1.6 l of ice water. After one hour, the precipitated solid is separated by suction filtration and washed with water and the product is dried in a vacuum.

Recrystallization from ethanol yields 26 g (52% of theoretical) of orange coloured crystals melting at 179.5°–180° C.

C$_{26}$H$_{28}$N$_6$O$_5$ (504.55)
Rf=0.28 (Solvent A)

(b)
6-[4-[4-(3-Aminopropyl)piperazin-1-yl]-3-nitro-phenyl]-5-methyl-4,5-dihydro-3(2H)-pyridazinone 32.0 g (64 mmol) of the phthalimido compound obtained as described under (a) are boiled under reflux with 30 ml of hydrazine hydrate (80% in water) in 700 ml of ethanol for 5 hours.

The ethanol is for the most part distilled off under vacuum and 200 ml of water are added to the residue which is then acidified to pH 2 with conc. hydrochloric acid.

The solid is removed by suction filtration and the filtrate is made alkaline (pH 12) and extracted with dichloromethane.

The organic phase is concentrated by evaporation and the residue is crystallized from isopropanol.

The yield is 16.0 g (67% of theoretical) of an orange-red powder, m.p. 110°–111° C.

C$_{18}$H$_{26}$N$_6$O$_3$ (374.45)
Rf=0.27 (Solvent C)

(c)
S-Methyl-N-[3-[4-[4-(4-methyl-6-oxo-1,4,5,6-tetrahydro pyridazin-3-yl)-2-nitro-phenyl]piperazin-1-yl]propyl]isothiourea hydriodide 11.23 g (30 mmol) of the amine obtained as described under (b) are boiled under reflux for 5 hours with 8.22 g (33 mmol) of dithiocarbamic acid-S,S-dimethylester hydriodide in 240 ml of acetonitrile.

The reaction mixture is concentrated by evaporation under vacuum and the residue is stirred up with 200 ml of ethyl acetate. After suction filtration, 17.2 g (100% of theoretical) of a red, amorphous powder is obtained which is sufficiently pure for further reaction.

C$_{20}$H$_{30}$IN$_7$O$_3$S (575.47)
Rf=0.4 (Solvent C)

(d)
N$^1$-[3-(1H-Imidazol-4-yl)propyl]-N$^3$-[3-[4-[4-(4-methyl-6-oxo-1,4,5,6-tetrahydro-pyridazin-3-yl)-2-nitro-phenyl]piperazin-1-yl]propyl]-guanidine 2.88 g (5 mmol) of the isothiouronium salt obtained as described under (c) are stirred up with 0.63 g (5 mmol) of 3-(1H-imidazol-4-yl)-propylamine in 10 ml of DMF for 12 hours at room temperature.

After the addition of 5 ml of a saturated aqueous potassium carbonate solution, the reaction mixture is extracted with dichloromethane/methanol (80/20 v/v). The organic phase is concentrated by evaporation and the residue is chormatographed on silica gel (Solvent D). The main fractions are combined and concentrated by evaporation and aqueous potassium carbonate solution is added to the residue which is then extracted with chloroform/methanol (80/20 v/v).

After concentration of the organic phases by evaporation, 0.32 g (12% of theoretical) of an orange-red foam having a softening range of 177°–119° C. is obtained.

C$_{25}$H$_{36}$N$_{10}$O$_3$ (524.63)
Rf=0.32 (Solvent D)

| $^1$H-NMR data (DMSO-d$_6$, TMS as internal standard) | δ = 1.05 | (d) | 3H |
|---|---|---|---|
| | 1.70 | (m) | 4H |
| | 2.1–2.9 | (m) | 6H |
| | 3.08 | (m) | 9H |
| | 3.36 | (m) | 4H |
| | 6.78 | (s) | 1H |
| | 7.31 | (d) | 1H |

| | | |
|---|---|---|
| 7.53 | (s) | 1H |
| 7.4–8.3 | (broad) | 1H, replaceable by D₂O, |
| 8.05 | (dd) | 1H |
| 8.14 | (d) | 1H |
| 9.2 | (broad) | 1H |
| and 11.8 | (broad) | 1H, replaceable by D₂O, |
| 11.03 | (s) | 1H ppm |

EXAMPLE 7

6-[4-[4-[3-(1H-Imidazol-4-yl)propylamino-carbonyl]-piperazin-1-yl]-3-nitro-phenyl]-4,5-dihydro-5-methyl-3(2H)pyridazinone

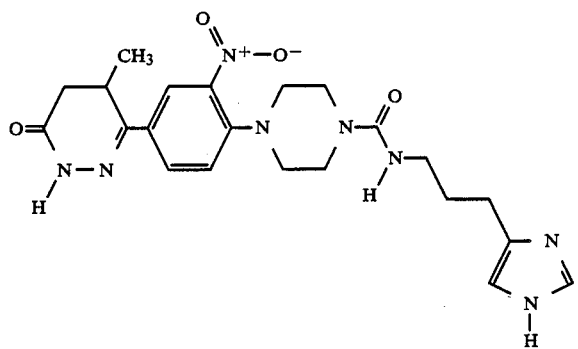

3.0 g (9.5 mmol) of 6-[4-(1-Piperazinyl)-3-nitro-phenyl]-4,5-dihydro-5-methyl-3(2H)-pyridazinone and 1.7 g (10.5 mmol) of carbonyl diimidazole are stirred together in 30 ml of DMF at room temperature for 2 hours. 1.88 g (15 mmol) of 3-(1H-imidazol-4-yl)-propylamine are then added and the reaction mixture is heated to 70° C. for 8 hours. After cooling, 10 ml of a saturated aqueous potassium carbonate solution are added and the reaction mixture is extracted with chloroform. The organic phase is concentrated by evaporation under vacuum and the residue is chromatographed on silica gel (Solvent F). Concentration of the main fractions by evaporation and crystallization of the residue yields 2.3 g (52% of theoretical) of orange crystals which have a melting point of 182° C.

C₂₂H₂₈N₈O₄ (468.52)
Rf=0.36 (Solvent F)

| ¹H-NMR data (DMSO-d₆, TMS as internal standard) | δ = 1.06 | (d) | 3H |
|---|---|---|---|
| | 1.70 | (q) | 2H |
| | 2.24 | (d) | 1H |
| | 2.45 | 3.4 | 2H |
| | 2.69 | (dd) | 1H |
| | 3.06 | (m) | 4H |
| | 3.4 | (m) | 7H |
| | 6.68 | (t) | 1H, replaceable by D₂O, |
| | 6.74 | (s) | 1H |
| | 7.36 | (d) | 1H |
| | 7.50 | (s) | 1H |
| | 7.96 | (dd) | 1H |
| | 11.04 | (s) | 1H |
| | 11.8 | (broad) | 1H, replaceable by D₂O, ppm |

EXAMPLE 8

6-[4-[4-[3-(1H-Imidazol-4-yl)propylamino-(ethoxycarbonyl)iminomethylene]piperazin-1-yl]-3-nitro-phenyl]-4,5-dihydro-5-methyl-3(2H)-pyridazinone

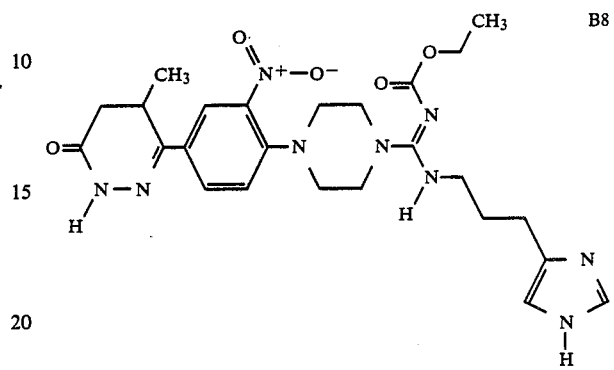

2.7 g (9.5 mmol) of N-Ethoxycarbonyl-imidocarbonic acid diphenylester are introduced into a suspension of 3.0 g (9.4 mmol) of 6-[3-nitro-4-(1-piperazinyl)-phenyl]-4,5-dihydro-5-methyl-3(2H)-pyridazinone in 30 ml of tetrahydrofuran. After 20 hours' stirring at room temperature, the solution is filtered and the filtrate is concentrated by evaporation under vacuum. The residue is taken up with 40 ml of acetonitrile. After the addition of 1.2 g (9.6 mmol) of 3-(1H-imidazol-4-yl)-propylamine, the mixture is boiled under reflux for 3.5 hours. The solution is concentrated by evaporation under vacuum and the residue obtained is chromatographed on silica gel, using solvent G. The orange coloured polar fraction is concentrated by evaporation under vacuum, the residue is taken up with 10 ml of saturated potassium carbonate solution and the aqueous phase is extracted with 3×10 ml of isopropanol. The combined organic phases yield 3.83 g (75%) of an orange-yellow, amorphous solid after dehydration with potassium carbonate, filtration and concentration by evaporation under vacuum.

C₂₅H₃₃N₉O₅ (539.60)
Rf=0.34 (Solvent D)

| ¹H NMR data (DMSO-d₆, TMS as internal standard) | δ = 1.04 | (d) | 3H |
|---|---|---|---|
| | 1.14 | (t) | 3H |
| | 1.78 | (m) | 2H |
| | 2.20–2.72 | (m) | 2H |
| | 2.49 | (t) | 2H |
| | 3.0–3.6 | (m) | 10H |
| | 3.78 | (quin) | 1H |
| | 3.91 | (q) | 2H |
| | 6.74 | (s) | 1H |
| | 7.34 | (d) | 1H |
| | 7.52 | (s) | 1H |
| | 7.96 | (dd) | 1H |
| | 8.19 | (d) | 1H ppm |

EXAMPLE 9

N[1]-[3-(1H-Imidazol-4-yl)propyl]-N[3]-[3-[4-(4-methyl-6-oxo-1,4,5,6-tetrahydropyridazin-3-yl)-2-nitro-anilino]-propyl]guanidine

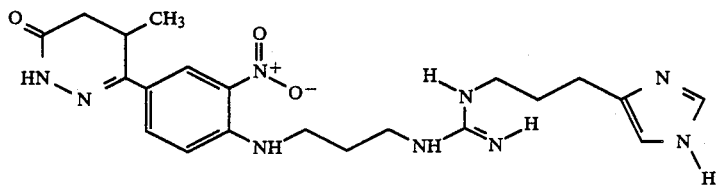

(a)
N[1]-Benzoyl-N[2]-[3-[4-(4-methyl-6-oxo-1,4,5,6-tetrahydropyridazin-3-yl)-2-nitro-anilino]propyl]-thiourea 7.51 g (70%) of an orange-yellow solid melting at 118°–120° C. are obtained in a manner analogous to Example 1(a) from 7.00 g (22.9 mmol) of N-[4-(4-methyl-6-oxo-1,4,5,6-tetrahydropyridazin-3-yl)-2-nitro-phenyl]-1,3-propane diamine and 3.75 g (23 mmol) of benzoyl isothiocyanate.

$C_{22}H_{24}N_6O_4$ (468.54)
Rf=0.93 (Solvent F)

(b)
N-[3-[4-(4-Methyl-6-oxo-1,4,5,6-tetrahydropyridazin-3-yl)-2-nitro-anilino]-propyl]-thiourea 4.0 g (69%) of an orange-yellow solid melting at 199°–203° C. are obtained analogously to Example 1(b) from 7.5 g (16.0 mmol) of the benzoyl thiourea prepared as described under (a).

$C_{15}H_{20}N_6O_3S$ (364.43)
Rf=0.53 (Solvent F)

(c)
N-[3-[4-(4-Methyl-6-oxo-1,4,5,6-tetrahydropyridazin-3-yl)-2-nitro-anilino]-propyl]-S-methyl-isothiuronium iodide 2.00 g (5.5 mmol) of the thiourea from stage (b) are methylated with 0.40 ml (6.4 mmol) of methyl iodide in a manner analogous to Example 1(c). 0.70 g (25%) of an orange-yellow solid melting at 152°–154° C. are obtained after recrystallization of the crude product from ethyl acetate/methanol (7:3).

$C_{16}H_{23}IN_6O_3S$ (506.37)
Rf=0.34 (Solvent G)

(d)
N[1]-[3-(1H-Imidazol-4-yl)propyl]-N[3]-[3-[4-(4-methyl-6-oxo-1,4,5,6-tetrahydropyridazin-3-yl)-2-nitro-anilino]-propyl]-guanidine 0.60 g (1.18 mmol) of the isothiuronium iodide obtained as under (c) are boiled under reflux with 0.15 g (1.19 mmol) of 3-(1H-imidazol-4-yl)-propylamine in 20 ml of dioxane for 4 hours. The residue obtained after concentration of the solution by evaporation under vacuum is chromatographed on silica gel, using solvent D. The product fractions are combined and concentrated by evaporation under vacuum and the residue is taken up with 10 ml of saturated potassium carbonate solution. 0.16 g (30%) of an orange-yellow, amorphous solid are obtained after extraction with 3×10 ml of isopropanol, dehydration of the combined organic phases and concentration by evaporation under vacuum.

$C_{21}H_{29}N_9O_3$ (455.52)
Rf=0.42 (Solvent D)

| $^1$H-NMR data (DMSO-$d_6$, TMS as internal standard) | δ= 1.05 | (d) | 3H |
|---|---|---|---|
| | 1.6–1.95 | (m) | 4H |
| | 2.1–3.6 | (m) | 11H |
| | 6.75 | (s) | 1H |
| | 7.18 | (d) | 1H |
| | 7.53 | (s) | 1H |
| | 7.95 | (dd) | 1H |
| | 8.38 | (d) | 1H |
| | 8.0 and 8.5 | (broad) | 6H, replaceable by D$_2$O, ppm. |
| | 11.8 | | |

EXAMPLE 10

N[1]-[3-(1H-Imidazol-4-yl)propyl]-N[3]-[1-[4-(4-methyl-6-oxo-1,4,5,6-tetrahydropyridazin-3 yl)-2-nitro-phenyl]-piperidin-4-yl]-guanidine

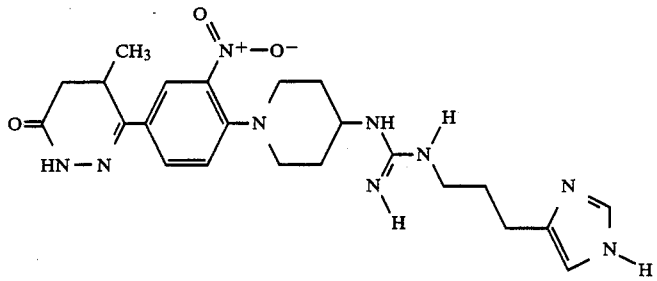

(a) N[1]-Benzoyl-N[2]-[1-[4-(4-methyl 6-oxo-1,4,5,6-tetrahydropyridazin-3-yl)-2-nitro-phenyl]-piperidin-4-yl]-thiourea 0.60 g (3.67 mmol) of benzoyl isothiocyanate in 5 ml of acetonitrile are added dropwise to a suspension of 1.20 g (3.62 mmol) of 6-[4-(4-aminopiperidin-1-yl)-3- nitro-phenyl]-4,5-dihydro-5-methyl-3(2H)-pyridazinone in 30 ml of acetonitrile. After 2 hours' stirring at room temperature, the precipitated solid is separated by suction filtration, washed with 10 ml of acetonitrile and dried under vacuum. 1.09 g (61%) of a yellow solid melting at 192°–194° C. are obtained.

$C_{24}H_{26}N_6O_4S$ (494.58)
Rf=0.68 (Solvent H)

(b) N-[1 [4-(4-Methyl-6-oxo-1,4,5,6-tetrahydropyridazin-3-yl)-2-nitro-phenyl]-piperidin-4-yl]-thiourea 0.73 g (93%) of a yellow solid melting at 222°–224° C. is obtained analogously to Example 1(b) by hydrolysis of 1.00 g (2.02 mmol) of the benzoylthiourea prepared as descried under (a).

$C_{17}H_{22}N_6O_3S$ (390.47)
Rf=0.58 (Solvent F)

(c) N-[1-[4-(4-Methyl-6-oxo-1,4,5,6-tetrahydropyridazin-3-yl)-2-nitro-phenyl]-piperidin-4-yl]-S-methyl-isothiuronium iodide 0.60 g (1.53 mmol) of the thiourea from stage (b) are stirred together with 0.11 ml (1.76 mmol) of methyl iodide in 30 ml of methanol at room temperature for 20 hours. The foam (0.85 g) obtained after removal of the solvent by evaporation under vacuum is TLC-pure and is used in the next stage without further working up.

$C_{18}H_{25}IN_6O_3S$ (532.41)
Rf=0.51 (Solvent F)

(d) $N^1$-[3-(1H-Imidazol-4-yl)propyl]-$N^3$-[1-[4 (4-methyl-6-oxo-1,4,5,6-tetrahydropyridazin 3-yl)-2-nitro-phenyl]piperidin-4-yl]-guanidine 0.75 g (1.41 mmol) of N-[1-[4-(4-Methyl-6-oxo-1,4,5,6-tetrahydropyridazin-3-yl)-2-nitro-phenyl]piperidin-4-yl]-S-methyl-isothiuronium iodide and 0.20 g (1.59 mmol) of 3-(1H-imidazol-4-yl)propylamine are together boiled under reflux in 30 ml of acetonitrile for 3 hours. The residue obtained after evaporation of the solvent under vacuum is chromatographically purified as in Example 9 (d). 0.57 g (84%) of an orange-yellow, amorphous solid is obtained.

$C_{23}H_{31}N_9O_3$ (481.56)
Rf=0.57 (Solvent D)

| $^1$H-NMR data (DMSO-d$_6$, TMS as internal standard) | δ = 1.05 | (d) | 3H |
|---|---|---|---|
| | 1.4–3.7 | (m) | 18H |
| | 6.77 | (s) | 1H |
| | 7.34 | (d) | 1H |
| | 7.54 | (s) | 1H |
| | 7.93 | (dd) | 1H |
| | 8.15 | (d) | 1H |
| | 8.4 | (broad) | 5H, replaceable by D$_2$O, ppm. |

EXAMPLE 11

6-[4-[4-[3-(1H-Imidazol-4-yl)-propylamino-iminomethylene]piperazin-1-yl]-3-nitro-phenyl]-5-hydroxymethyl-4,5-dihydro-3(2H)-pyridazinone

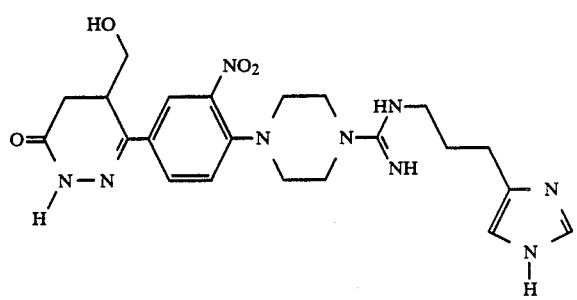

The title compound is obtained in a manner analogous to Example 3(d) from 1.60 g (3 mmol) of 6-[4-[4-(methylthioiminomethylene)-piperazin-1-yl]-3-nitro-phenyl]-4,5-dihydro-5-hydroxymethyl-3(2H)-pyridazinone and 0.40 g (3.4 mmol) of 3-(1H-imidazol-4-yl)-propylamine in 8 ml of dimethylformamide.

The crude product is chromatographically purified on silica gel with Solvent E and recrystallized from ethanol. 0.22 g (15%) of orange-yellow crystals melting at 196.7°–197 3° C. are obtained.

$C_{22}H_{29}N_9O_4$ (483.53)
Rf=0.22 (Solvent D)

| $^1$H-NMR data (DMSO-d$_6$, TMS as internal standard) | δ = 1.73 | (quin) | 2H |
|---|---|---|---|
| | 2.43–2.75 | (m) | 4H |
| | 2.96 | (t) | 4H |
| | 3.0–3.4 | (m) | 12H, 1H replaceable by D$_2$O |
| | 6.69 | (s) | 1H |
| | 7.33 | (d) | 1H |
| | 7.48 | (s) | 1H |
| | 7.95 | (dd) | 1H |
| | 8.17 | (d) | 1H, ppm. |

EXAMPLE 12

6-[3-Fluoro-4-[4-[3-(1H-imidazol-4-yl)-propylamino-iminomethylene]-piperazin-1-yl]-phenyl]-4,5-dihydro-5-methyl-3(2H)-pyridazinone

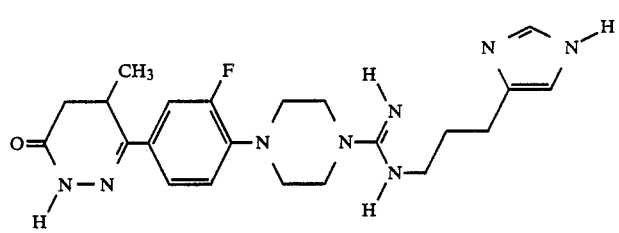

0.54 g (67%) of a pale yellowish, amorphous solid is obtained in a manner analogous to Example 3(d) from 0.90 g (1.83 mmol) of 6-[3-fluoro-4-[4-(methylthioiminomethylene) piperazin-1-yl]-phenyl]-4,5-dihydro-5-methyl-3(2H)-pyridazinone hydriodide and 0.23 g (1.83 mmol) of 3-(1H-imidazol-4-yl)-propylamine after chromatographic purification of the crude product on silica gel, using Solvent D.

$C_{22}H_{29}FN_8O$ (440.53)
Rf=0.50 (Solvent D)

| $^1$H-NMR data (DMSO-$d_6$, TMS as internal standard) | δ = 1.11 | (d) | 3H |
|---|---|---|---|
| | 1.78 | (quin) | 2H |
| | 2.33–2.67 | (m) | 4H |
| | 2.9–3.5 | (m) | 11H |
| | 6.75 | (s) | 1H |
| | 7.06 | (t) | 1H |
| | 7.40–7.58 | (m) | 4H, 1H replaceable by D$_2$O, |
| | 7.9 | (broad) | 2H, replaceable by D$_2$O |
| | 10.8 | (broad) | 1H, replaceable by D$_2$O, ppm. |

EXAMPLE 13

6-[3-Cyano-4-[4-[3-(1H-imidazol-4-yl)-propylamino-iminomethylene]-piperazin-1-yl]-phenyl]-4,5-dihydro-3(2H)-pyridazinone

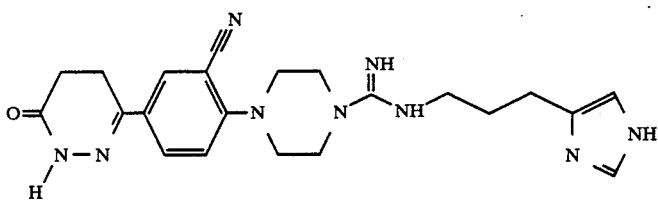

1.00 g (2.1 mmol) of 6-[3-Cyano-4-[4-(methylthio-iminomethylene)-piperazin-1-yl]-phenyl]-4,5-dihydro-3(2H)pyridazinone hydriodide and 0.36 g (2.88 mmol) of 3-(1H-imidazol-4-yl)-propylamine are boiled under reflux for 11 hours in 20 ml of acetonitrile and 10 ml of dimethylformamide.

After evaporation of the solvent under vacuum, the residue obtained is chromatographed on silica gel, using Solvent G. The residue obtained from the main fraction after evaporation is taken up with 10 ml of saturated potassium carbonate solution.

0.52 g (57%) of a colourless solid of m.p.263.8°–265.6° C. (decomposition) crystallize.

$C_{22}H_{27}N_9O$ (433.52)
Rf=0.25 (Solvent E)

| $^1$H-NMR data (DMSO-$d_6$, TMS as internal standard) | δ = 1.85 | (m) | 2H |
|---|---|---|---|
| | 2.31–2.63 | (m) | 4H |
| | 2.95 | (t) | 2H |
| | 3.0–3.8 | (m) | 10H |
| | 6.83 | (s) | 1H |
| | 7.23 | (d) | 1H |
| | 7.59 | (s) | 1H |
| | 7.95–8.04 | (s + d) | 2H |
| | 8.7 | (broad) | 2H, replaceable by D$_2$O |
| | 11.0 | (s) | 1H, replaceable by D$_2$O, ppm. |

EXAMPLE 14

6-[3-Cyano-4-[4-[3-(1H-imidazol-4-yl)-propylamino-iminomethylene]-piperazin-1-yl]-phenyl]-4,5-dihydro-5-methyl-3(2H)-pyridazinone

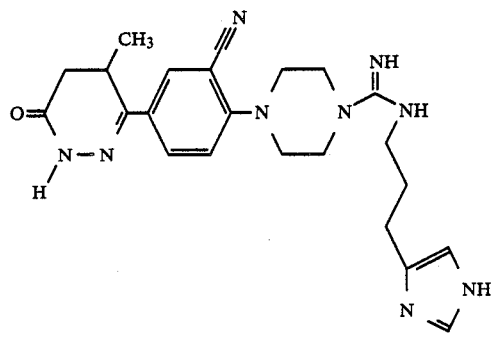

0.47 ml (7.5 mmol) of Methyl iodide are added to a solution of 1.80 g (5 mmol) of 6-[3-cyano-4-[4-(aminothiocarbonyl)-piperazin-1-yl]-phenyl]-4,5-dihydro-5-methyl-3(2H)-pyridazinone in 30 ml of dimethylformamide and the reaction mixture is stirred at room temperature.

0.69 g (5.5 mol) of 3-(1H-imidazol-4-yl)-propylamine are added after 16 hours and the solution continues to be stirred for 2 days. 20 ml of a 10% aqueous potassium carbonate solution are added and the reaction mixture is extracted with 3×20 ml of chloroform/methanol (80/20 v/v). After dehydration and concentration of the organic phases by evaporation under vacuum, the residue is chromatographed on silica gel, using Solvent E. The main fraction which has been concentrated by evaporation is crystallized with ethyl acetate.

1.12 g (50%) of a colourless solid is obtained, which contains about ⅓ mol of ethyl acetate according to the NMR spectrum and begins to melt at 140° C. without a sharp melting point.

$C_{23}H_{29}N_9O$ (447.55)
Rf=0.37 (Solvent D)

| $^1$H-NMR data (DMSO-$d_6$, TMS as internal standard) | δ = 1.05 | (d) | 3H |
|---|---|---|---|
| | 1.80 | (quin) | 2H |
| | 2.11–2.78 | (m) | 4H |
| | 3.0–3.7 | (m) | 11H |
| | 6.73 | (s) | 1H |
| | 7.21 | (d) | 1H |
| | 7.50 | (s) | 1H |
| | 7.96–8.06 | (m) | 2H |
| | 9.1 | (broad) | 2H, replaceable by D$_2$O |
| | 11.1 | (broad) | 1H, replaceable by D$_2$O, ppm. |

EXAMPLE 15

N¹-[3-(1H-Imidazol-4-yl)propyl]-N³-[1-[4-(4-hydroxymethyl-6-oxo-1,4,5,6-tetrahydropyridazin-3-yl)-2-nitro-phenyl]-piperidin-4-yl]-guanidine

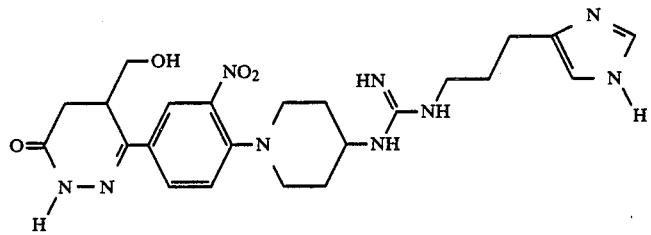

2.11 g (4.1 mmol) of N-[1-[4-(4-hydroxymethyl-6-oxo-1,4,5,6-tetrahydropyridazin-3-yl)-2-nitro-phenyl]-piperidin-4-yl]-S-methyl-isothiuronium iodide and 0.57 g (4.5 mmol) of 3-(1H-imidazol-4-yl)-propylamine are stirred in 50 ml of dimethylformamide for 9 hours at 90° C. When the reaction mixture has been substantially concentrated by evaporation under vacuum, the residue is taken up with 70 ml of dichloromethane/methanol (80/20 v/v) and extracted with 20 ml of a 50% potassium carbonate solution.

The organic phase is dehydrated with sodium sulphate, filtered and concentrated by evaporation under vacuum. The solid obtained after chromatographic purification on silica gel with Solvent E is crystallized from acetonitrile. 0.52 g (25%) of an orange powder, m.p. 135°–137° C., are obtained.

$C_{23}H_{31}N_9O_4$ (497.56)

Rf=0.28 (Solvent E)

| ¹H-NMR data (DMSO-d₆, TMS as internal standard) | δ = 1.45–2.0 | (m) | 6H |
|---|---|---|---|
| | 2.2–2.8 | (m) | 4H |
| | 2.93 | (t) | 2H |
| | 3.05–3.72 (m) | | 9H, |
| | 1H replaceable by D₂O | | |
| | 6.78 | (s) | 1H |
| | 7.32 | (d) | 1H |
| | 7.54 | (s) | 1H |
| | 7.8 | (broad) | 3H, |
| | replaceable by D₂O | | |
| | 7.94 | (dd) | 1H |
| | 8.16 | (d) | 1H, |
| | ppm. | | |

EXAMPLE 16

N¹-[3-(1H-Imidazol-4-yl)propyl-N³-[[1-4-(4-methyl-6-oxo-1,4,5,6-tetrahydropyridazin-3-yl)-2-nitro-phenyl]-piperidin-4yl]-methyl]-guanidine

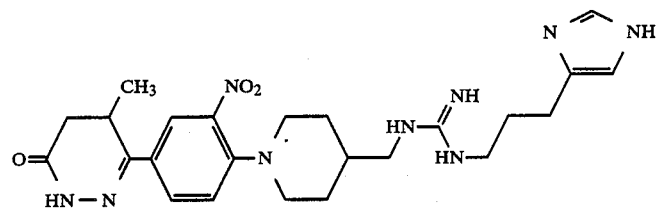

1.20 g (2.2 mmol) of S-methyl-N-[[1-[4-(4-methyl-6-oxo-1,4,5,6-tetrahydropyridazin-3-yl)-2-nitro-phenyl]-piperidin-4-yl]methyl]-isothiuronium iodide and 0.30 g (2.4 mmol) of 3-(1H-imidazol-4-yl)-propylamine are boiled under reflux in 30 ml of pyridine for 3 hours.

The residue obtained after evaporation of the solvent under vacuum is chromatographically purified as in Example 1(d). 0.57 g (53%) of an orange-yellow solid are obtained.

$C_{24}H_{33}N_9O_3$ (495.59)

Rf=0.57 (Solvent D)

| ¹H-NMR data (DMSO-d₆, TMS as internal standard) | δ = 1.04 | (d) | 3H |
|---|---|---|---|
| | 1.2–3.5 | (m) | 20H |
| | 6.76 | (s) | 1H |
| | 7.31 | (d) | 1H |
| | 7.53 | (s) | 1H |
| | 7.92 | (dd) | 1H |
| | 8.12 | (d) | 1H |
| | 8.4 | (broad) | 5H, |
| | replaceable by D₂O, | | |
| | ppm. | | |

EXAMPLE 17

N[1]-[3-(1H-imidazol-4-yl)propyl]-N[3]-[1-[4-(6-oxo-1,4,5,6-tetrahydropyridazin-3-yl)-2-cyano-phenyl]-piperidin-4-yl]-guanidine

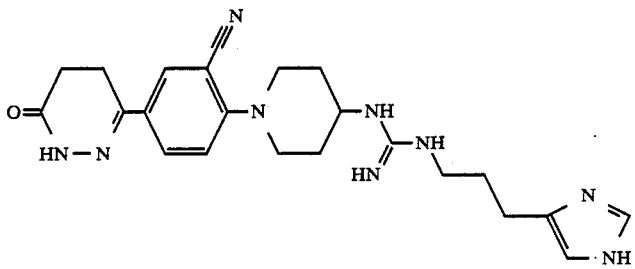

0.36 g (40%) of a pale beige solid melting at 144°–148° C. are obtained from 1.00 g (2.0 mmol) of N-[1-2-cyano-4-(6-oxo-1,4,5,6-tetrahydropyridazin-3-yl)-phenyl]-piperidin- 4-yl]-S-methyl-isothiuronium iodide and 0.25 g (2.0 mmol) of 3-(1H-imidazol-4-yl)propylamine in a manner analogous to Example 13 after chromatographic purification on silica gel, using solvent G, and crystallization with isopropanol/ethyl acetate.

$C_{23}H_{29}N_9O$ (447.55)
Rf=0.33 (Solvent E)

| $^1$H-NMR data (DMSO-d$_6$, TMS as internal standard) | δ = | 1.4–2.1 | (m) | 6H |
|---|---|---|---|---|
| | | 2.28–2.6 | (m) | 4H |
| | | 2.8–3.8 | (m) | 9H |
| | | 6.77 | (s) | 1H |
| | | 7.20 | (d) | 1H |
| | | 7.53 | (s) | 1H |
| | | 7.85–7.98 | (m) | 2H |
| | | 8.6 replaceable by D$_2$O, ppm. | (broad) | 4H, |

EXAMPLE 18 N[1]-[3-(1H-Imidazol 4-yl)propyl]-N[3]-[4-[4-(4-methyl-6-oxo-4,5,6-tetrahydropyridazin-3-yl)-2-nitro-anilino]butyl]guanidine

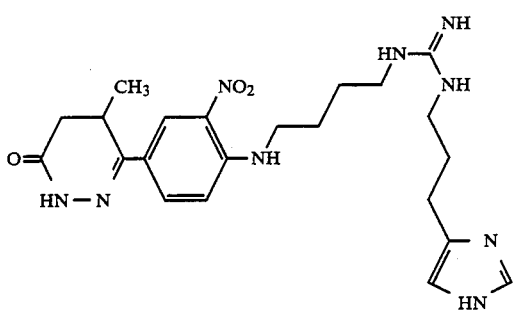

0.50 g (39%) of the title compound is obtained in the form of an orange coloured, amorphous solid from 1.40 g (2.70 mmol) of N-[4-[4-(4-methyl-6-oxo-1,4,5,6-tetrahydropyridazin-3-yl)-2-nitro-anilino]butyl]-S-methylisothiuronium iodide and 0.34 g (2.7 mmol) of 3-(1H-imidazol-4-yl)-propylamine in a manner analogous to Example 1(d).

$C_{22}H_{31}N_9O_3$ (469.55)
Rf=0.48 (Solvent D)

| $^1$H-NMR data (DMSO-d$_6$, | δ = | 1.06 | (d) | 3H |
|---|---|---|---|---|
| TMS as internal standard) | | 1.4–1.9 | (m) | 6H |
| | | 2.15–2.80 | (m) | 4H |
| | | 2.95–3.53 | (m) | 7H |
| | | 6.76 | (s) | 1H |
| | | 7.14 | (d) | 1H |
| | | 7.54 | (s) | 1H |
| | | 7.95 | (dd) | 1H |
| | | 8.37 | (d) | 1H |
| | | 8.5 replaceable by D$_2$O, ppm. | (broad) | 5H, |

EXAMPLE 19

N[1]-[3-(1H-Imidazol-4-yl)propyl]-N[3]-[3-[4-(4-methyl-6-oxo-1,4,5,6-tetrahydropyridazin-3-yl)-2-nitro-phenyl]-propyl]guanidine

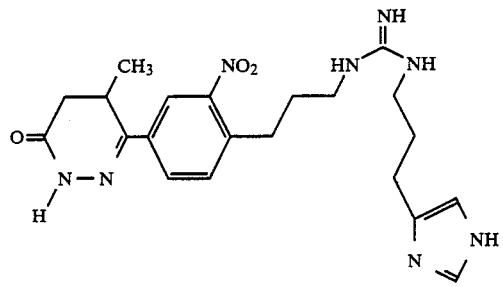

2.0 g (4 mmol) of N-[3-[4-(4-Methyl-6-oxo-1,4,5,6-tetrahydropyridazin-3-yl)-2-nitro-phenyl]propyl]-S-methyl-isothiuronium iodide and 0.5 g (4 mmol) of 3-(1H-imidazol-4-yl)propylamine are stirred together in 15 ml of dimethylformamide for 2 days at room temperature.

After evaporation of the solvent in a medium high vacuum 10 ml of saturated potassium carbonate solution are added to the residue which is then extracted with 3×20 ml of chloroform/methanol (80/20 v/v).

The residue obtained after evaporation of the solvents under vacuum is chromatographically purified on silica gel, using Solvent D.

After working up of the product in a manner analogous to Example 1(d), 0.46 g (26%) of a yellowish beige powder melting in the range of 96°–99° C. are obtained. According to 1H-NMR, this product contains ⅓ mol of crystal ethanol.

$C_{21}H_{28}N_8O_3 \times ⅓ C_2H_6O$ (440 51)
Rf=0.36 (Solvent D)

| $^1$H-NMR data (DMSO-d$_6$, as internal standard) | δ = | 1.03–1.23 | (m) | 3H +3H (EtOH) |
|---|---|---|---|---|
| | | 1.60–1.90 | (m) | 4H |
| | | 2.4–2.75 | (m) | 4H |
| | | 2.87 | (t) | 2H |

-continued

| | | |
|---|---|---|
| 3.03–3.3 | (m) | 5H |
| 3.38 | (q) 2H (EtOH) | |
| 6.76 | (s) | 1H |
| 7.52 | (s) | 1H |
| 7.59 | (d) | 1H |
| 8.00 | (dd) | 1H |
| 8.23 | (d) | 1H |
| 8.6 | (broad) | 4H, replaceable by D$_2$O, ppm. |

EXAMPLE 20

$N^1$-[3-(1H-Imidazol-4-yl)propyl]-$N^3$-[3-[4-(4-hydroxymethyl-6-oxo-1,4,5,6-tetrahydropyridazin-3-yl)-2-nitro-anilino]propyl]-guanidine

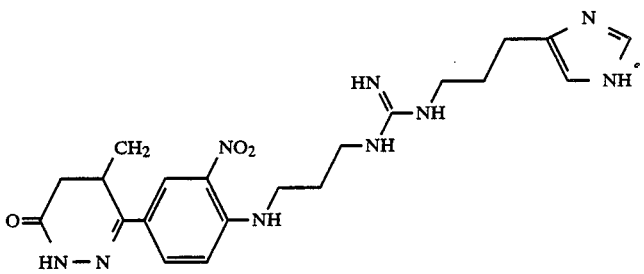

1.50 g (6 mmol) of dithiocarbamic acid-S,S-dimethylester. hydriodide are added to a solution of 1.93 g (6 mmol) of N-[4-(4-hydroxymethyl-6-oxo-1,4,5,6-tetrahydropyridazin-3-yl)-2-nitro-phenyl]-1,3-propanediamine in 10 ml of dimethylformamide.

1.12 g (9 mmol) of 3-(1H-Imidazol 4-yl)-propylamine are added after 2 days' stirring at room temperature and stirring of the reaction mixture is continued for 12 hours.

After the reaction mixture has been worked up in a manner analogous to Example 19 (Solvent G), 1.10 g (39%) of an orange coloured, amorphous powder having a melting range of from 113°–116° C. are obtained.

$C_{21}H_{29}N_9O_4$ (471.52)
Rf=0.24 (Solvent G)

| $^1$H-NMR data (DMSO-d$_6$, TMS as internal standard) | δ = 1.6–2.0 | (m) | 4H |
|---|---|---|---|
| | 2.4–2.7 | (m) | 4H |
| | 3.1–3.6 | (m) | 10H, 1H replaceable by D$_2$O, |
| | 6.79 | (s) | 1H |
| | 7.21 | (d) | 1H |
| | 7.55 | (s) | 1H |
| | 7.98 | (dd) | 1H |
| | 8.43 | (d) | 1H |
| | 8.5 | (broad) | 5H, replaceable by D$_2$O, ppm. |

EXAMPLE 21

$N^1$-[3-(1H-Imidazol-4-yl)propyl]-$N^2$-[2-[4(4-methyl-6-oxo-1,4,5,6-tetrahydropyridazin-3-yl)-2-nitro-anilino]ethyl]urea

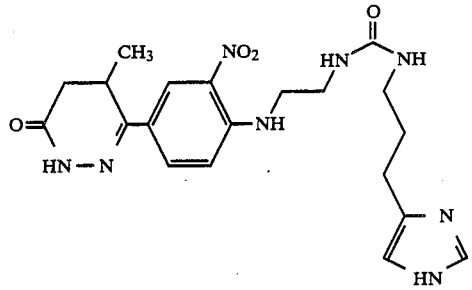

1.11 g (6.84 mmol), of carbonyldiimidazole are added to a suspension of 1.98 g (6.8 mmol) of N-[4-(4-methyl-6-oxo-1,4,5,6-tetrahydropyridazin-3-yl)-2-nitro-phenyl]ethylene diamine in 40 ml of dioxane and the reaction mixture is stirred at room temperature for 5 hours.

0.85 g (6.8 mmol) of 3-(1H-imidazol-4-yl)-propylamine are added and the suspension is then boiled under reflux for 3 hours. 30 ml of water are added to the cooled reaction mixture, the precipitated solid is suction filtered and the filtrate is extracted with 3×30 ml of dichloromethane/methanol (90/10 v/v).

The solid obtained after concentration of the combined organic phases by evaporation under vacuum is recrystallized twice from methanol. 0.35 g (12%) of orange-yellow crystals melting at 177°–178° C. are obtained.

$C_{20}H_{26}N_8O_4$ (442.48)
Rf=0.64 (Solvent F)

| $^1$H-NMR data (DMSO-d$_6$, TMS as internal standard) | δ = 1.06 | (d) | 3H |
|---|---|---|---|
| | 1.65 | (quin) | 2H |
| | 2.16–2.82 | (m) | 4H |
| | 2.9–3.6 | (m) | 7H |
| | 6.08 | (t) | 1H, replaceable by D$_2$O |
| | 6.17 | (broad) | 1H, replaceable by D$_2$O |
| | 6.73 | (s) | 1H |
| | 7.22 | (d) | 1H |
| | 7.51 | (s) | 1H |
| | 7.95 | (dd) | 1H |
| | 8.39 | (d) | 1H |
| | 8.51 | (t) | 1H, replaceable by D$_2$O |
| | 10.96 | (s) | 1H, replaceable by D$_2$O |
| | 11.7 | (broad) | 1H, replaceable by D$_2$O |

EXAMPLE 22

N[1]-[3-(1H-Imidazol-4-yl)propyl]-N[2]-[3-[4-(4-methyl-6-oxo-1,4,5,6-tetrahydropyridazin-3-yl)-2-nitro-anilino]-propyl]urea

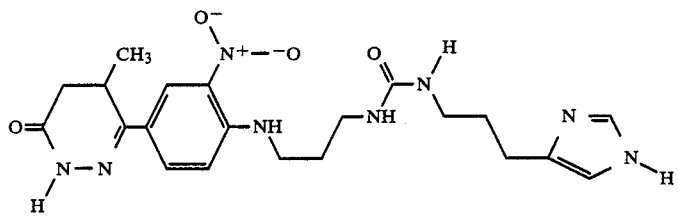

51 g (17%) of an orange-yellow solid melting at 177°–179° C. are obtained in a manner analogous to Example 21 from 2.0 g (6.5 mmol) of N-[4-(4-methyl-6-oxo-1,4,5,6-tetrahydropyridazin-3-yl)-2-nitro-phenyl]-1,3-propanediamine, 1.06 g (6.5 mmol) of carbonyldiimidazole and 0.82 g (6.5 mmol) of 3-(1H-imidazol-4-yl)-propylamine after chromatographic purification of the crude product on silica gel using dichloromethane/methanol/conc.ammonia (90:9:1) as solvent, followed by recrystallization from methanol.

$C_{21}H_{28}N_8O_4$ (456.51)

Rf=0.30 (dichloromethane/methanol/conc.ammonia 90:9:1)

| $^1$H-NMR data (DMSO-d[6], TMS as internal standard) | δ = 1.07 | (d) | 3H |
|---|---|---|---|
| | 1.56–1.82 | (m) | 4H |
| | 2.17–2.76 | (m) | 4H |
| | 2.9–3.5 | (m) | 7H |
| | 5.95 replaceable by D$_2$O | (t) | 1H |
| | 6.01 replaceable by D$_2$O | (t) | 1H, |
| | 6.73 | (s) | 1H |
| | 7.13 | (d) | 1H |
| | 7.50 | (s) | 1H |
| | 7.96 | (dd) | 1H |
| | 8.39 | (d) | 1H |
| | 9.47 replaceable by D$_2$O | (t) | 1H, |
| | 10.94 replaceable by D$_2$O | (s) | 1H, |
| | 11.8 replaceable by D$_2$O, ppm. | (broad) | 1H, |

EXAMPLE 23

N[2]-Benzoyl-N[1]-[3-(1H-imidazol-4-yl)propyl]-N[3]-[1-[4-(4-methyl-6-oxo-1,4,5,6-tetrahydropyridazin-3-yl)-2-nitro-phenyl]-piperidin-4-yl]-guanidine

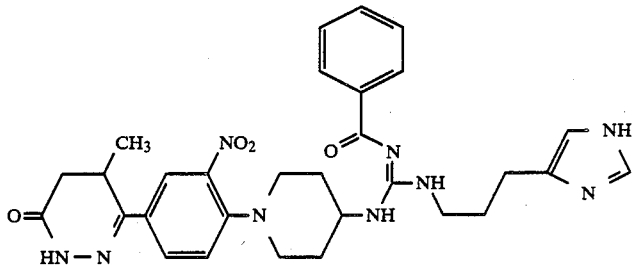

1.70 g (5.13 mmol) of 6-[4-(4-Amino-piperidin-1-yl)-3-nitro-phenyl]-4,5-dihydro-5-methyl-3(2H)-pyridazinone are reacted with 1.60 g (5.04 mmol) of N-benzoylimidocarbonic acid-diphenylester and 0.65 g (5.2 mmol) of 3-(1H-imidazol-4-yl)-propylamine in a manner analogous to Example 8.

The crude product is dissolved in 15 ml of methoxyethanol at boiling point and precipitated by the addition of 20 ml of methanol after the solution has cooled to room temperature.

0.58 g (20%) of orange-yellow crystals, m.p. 192°–193° C., are obtained.

$C_{30}H_{35}N_9O_4$ (585.67)

Rf=0.43 (dichloromethane:methanol:conc.ammonia 90:10:1)

| $^1$H-NMR data (CD$_3$OD, TMS as internal standard) | δ = 1.17 | (d) | 3H |
|---|---|---|---|
| | 1.67–2.10 | (m) | 6H |
| | 2.32–2.86 | (m) | 4H |
| | 3.06 | (t) | 2H |
| | 3.1–3.7 | (m) | 6H |
| | 4.9 replaceable by D$_2$O | (broad) | 4H, |
| | 6.83 | (s) | 1H |
| | 7.28–7.53 | (m) | 4H |
| | 7.57 | (s) | 1H |
| | 7.96 | (dd) | 1H |
| | 8.02–8.17 | (m) | 2H |
| | 8.20 ppm. | (d) | 1H, |

EXAMPLE 24

N²-Ethoxycarbonyl-N¹-[3-(1H-imidazol-4-yl)propyl]-N³-[1-[4-(4-methyl-6-oxo-1,4,5,6-tetrahydropyridazin-3-yl)-2-nitro-phenyl]-piperidin-4-yl]-guanidine

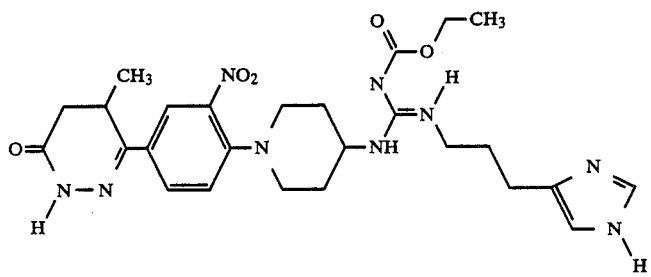

(a)
N¹-Ethoxycarbonyl-N²-[1-[4-(4-methyl-6-oxo-1,4,5,6-tetrahydropyridazin-3-yl)-2-nitro-phenyl]-piperidin-4-yl]-S-methyl-isothiourea 1.18 ml (8.46 mmol) of triethylamine are slowly added to a suspension of 0.90 g (1.69 mmol) of N-[1-[4-(4-methyl-6-oxo-1,4,5,6-tetrahydropyridazin3-yl)-2-nitro-phenyl]-piperidin-4-yl]-S-methyl-isothiuronium iodide in 20 ml of dichloromethane and the reaction mixture is stirred for 10 minutes.

0.20 ml (2.09 mmol) of ethylchloroformate in 10 ml of dichloromethane are added dropwise to the resulting solution. The solution is then stirred at room temperature for 2 hours and washed twice with 10 ml of water.

After dehydration of the organic phase and concentration by evaporation under vacuum, an orange-yellow solid which melts at 193°–195° C. after recrystallization from 15 ml of ethyl acetate is obtained.

Yield: 0.70 g (87%)
$C_{21}H_{28}N_6O_5S$ (476.56)
Rf=0.64 (Solvent H)

(b)
N²-Ethoxycarbonyl-N¹-[3-(1H-imidazol-4-yl)propyl]-N³-[1-[4-(4-methyl-6-oxo-1,4,5,6-tetrahydropyridazin-3-yl)-2-nitro-phenyl]-piperidin-4-yl]-guanidine 0.65 g (1.36 mmol) of the compound obtained as described under (a) and 0.38 g (3.04 mmol) of 3-(1H-imidazol-4-yl)-propylamine are boiled under reflux in 20 ml of acetonitrile for 8 hours.

The residue obtained after evaporation of the solvent under vacuum is chromatographed on silica gel, using dichloromethane:methanol:conc.ammonia (90:10:1) as solvent.

The polar, orange coloured main fraction yields 0.19 g (26%) of an orange-yellow, amorphous solid after concentration by evaporation under vacuum.

$C_{26}H_{35}N_9O_5$ (553.63)
Rf=0.36 (dichloromethane:methanol:conc.ammonia 90:10:1)

| ¹H-NMR data (CDCl₃, TMS as internal standard) | δ = | | |
|---|---|---|---|
| | 1.24 | (d) | 3H |
| | 1.31 | (t) | 3H |
| | 1.7–2.2 | (m) | 6H |
| | 2.40–2.81 | (m) | 4H |
| | 2.94–3.10 | (m) | 2H |
| | 3.2–3.5 | (m) | 6H |
| | 4.12 | (q) | 2H |
| | 4.2 | (broad) | 1H, replaceable by D₂O |
| | 6.81 | (s) | 1H |
| | 7.11 | (d) | 1H |
| | 7.68 | (s, broad) | 1H |
| | 7.87 | (dd) | 1H |
| | 8.17 | (d) | 1H |
| | 9.0 | (s) | 1H, replaceable by D₂O |
| | 9.2 | (broad) | 1H, replaceable by D₂O, ppm. |

We claim:

1. 6-Oxo-pyridazine derivative corresponding to formula I:

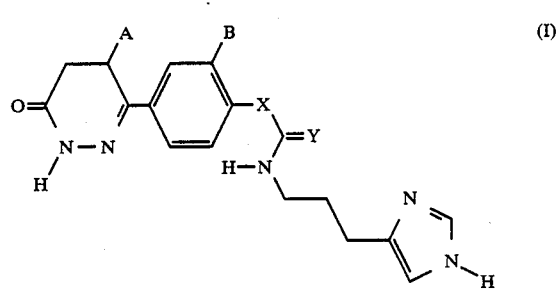

wherein A represents a hydrogen atom, a C₁–C₃-alkyl group or a hydroxymethyl group, B represents a hydrogen atom, a halogen atom, a cyano group or a nitro group, X represents a group corresponding to one of the following formulae:

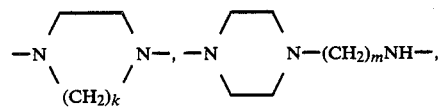

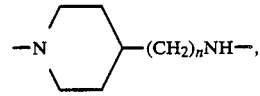

—NH(CH₂)ₘNH—,   —O(CH₂)ₙNH—   or —(CH₂)ₙNH— wherein k has the value 1, 2 or 3, m has the value 2, 3, 4, 5 or 6 and n has the value 0, 1, 2, 3 or 4, and Y represents an oxygen atom, a group corresponding to one of the following formulae =NH, =N—CN,

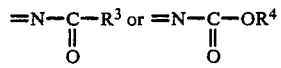

wherein R³ represents a straight chain or branched C₁–C₆-alkyl group or an aryl group which is unsubstituted or substituted with one or more halogen atoms, C₁–C₃-alkyl groups or C₁–C₃-alkoxy groups and R⁴ represents a straight chain or branched C₁–C₄-alkyl group unsubstituted or substituted with one or more halogen atoms, C₁–C₃-alkoxy groups or phenyl groups, or physiologically acceptable salt thereof.

2. The 6-oxo-pyridazine derivative according to claim 1, wherein A represents a hydrogen atom, a C₁–C₃-alkyl group or a hydroxymethyl group, B represents a hydrogen atom, a halogen atom, a cyano group or a nitro group and X represents a group of the formula

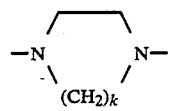

wherein k has the value 1, 2 or 3, and Y represents an oxygen atom or the group =NH.

3. The 6-oxo-pyridazine derivative according to claim 1, wherein A represents a hydrogen atom, a C₁–C₃-alkyl group or a hydroxymethyl group, B represents a hydrogen atom, a halogen atom, a cyano group or a nitro group, X represents a group of the formula

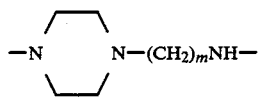

wherein m has the value 2, 3, 4, 5 or 6 and Y represents an oxygen atom or the group =NH.

4. The 6-oxo-pyridazine derivative according to claim 1, wherein A represents a hydrogen atom, a C₁–C₃-alkyl group or a hydroxymethyl group, B represents a hydrogen atom, a halogen atom, a cyano group or a nitro group, X represents a group of the formula

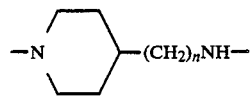

wherein n has the value 0, 1, 2, 3 or 4, and Y represents an oxygen atom or the group =NH.

5. The 6-oxo-pyridazine derivative according to claim 1, wherein A represents a hydrogen atom, a C₁–C₃-alkyl group or a hydroxymethyl group, B represents a hydrogen atom, a halogen atom, a cyano group or a nitro group, X represents a group of the formula —NH(CH₂)$_m$NH— wherein m has the value 2, 3, 4, 5 or 6, and Y represents an oxygen atom or the group =NH.

6. The 6-oxo-pyridazine derivative according to claim 1, wherein A represents a hydrogen atom, a C₁–C₃-alkyl group or a hydroxymethyl group, B represents a hydrogen atom, a halogen atom, a cyano group or a nitro group, X represents a group corresponding to one of the following formulae;

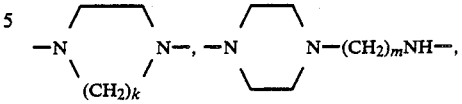

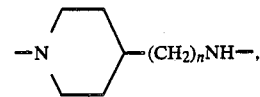

—NH—(CH₂)$_m$NH—,  —O(CH₂)$_n$NH—  or —(CH₂)$_n$NH— wherein k has the value 1, 2 or 3, m has the value 2, 3, 4, 5 or 6 and n has the value 0, 1, 2, 3 or 4, and Y represents a group of the formula

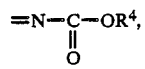

wherein R⁴ stands for a straight chain or branched C₁–C₄-alkyl group unsubstituted or substituted with one or more halogen atoms, C₁–C₃-alkoxy groups or phenyl groups.

7. 6-[4-[4-[3-(1H-Imidazol-4-yl)-propylamino-iminomethylene]-piperazin-1-yl]-3-nitro-phenyl]-4,5-dihydro-5-methyl-3(2H)-pyridazinone.

8. N¹-[3-(1H-Imidazol-4-yl)propyl]-N³-[3-[4-[4-(4-methyl-6-oxo-1,4,5,6-tetrahydropyridazin-3-yl)-2-nitro-phenyl]-piperazin-1-yl)propyl]-guanidine.

9. N¹-[3-(1H-Imidazol-4-yl)propyl]-N³-[2-[4-(4-methyl-6-oxo-1,4,5,6-tetrahydropyridazin-3-yl)-2-nitro-anilino]-ethyl]-guanidine.

10. A cardiotonic pharmaceutical composition comprising a cardiotonically effective amount of a 6-oxo-pyridazine derivative corresponding to formula I:

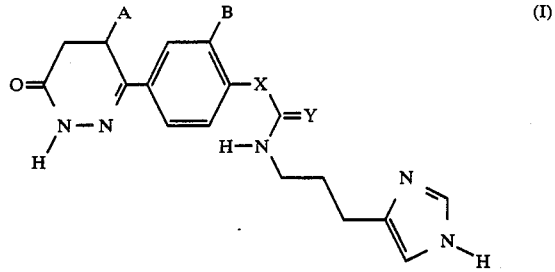

wherein A represents a hydrogen atom, a C₁–C₃-alkyl group or a hydroxymethyl group, B represents a hydrogen atom, a halogen atom, a cyano group or a nitro group, X represents a group corresponding to one of the following formulae:

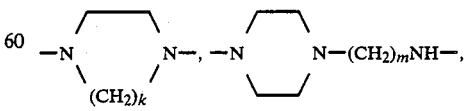

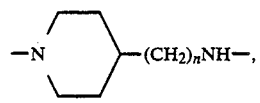

—NH(CH₂)ₘNH—, —O(CH₂)ₙNH— or —(CH₂)ₙNH— wherein k has the value 1, 2 or 3, m has the value 2, 3, 4, 5 or 6 and n has the value 0, 1, 2, 3 or 4, and Y represents an oxygen atom, a group corresponding to one of the following formulae =NH, =N—CN,

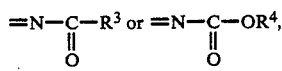

wherein R³ represents a straight chain or branched C₁-C₆-alkyl group or an aryl group which is unsubstituted or substituted with one or more halogen atoms, C₁-C₃-alkyl groups or C₁-C₃-alkoxy groups and R⁴ represents a straight chain or branched C₁-C₄-alkyl group unsubstituted or substituted with one or more halogen atoms, C₁-C₃-alkoxy groups or phenyl groups, or physiologically acceptable groups or phenyl groups, or physiologically acceptable salt thereof and a pharmaceutically acceptable carrier therefor.

11. The pharmaceutical composition according to claim 10, wherein A represents a hydrogen atom, a C₁-C₃-alkyl group or a hydroxymethyl group, P represents a hydrogen atom, a halogen atom, a cyano group or a nitro group and X represents a group of the formula

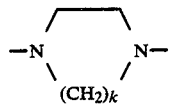

wherein K has the value 1, 2 or 3, and Y represents an oxygen atom or the group =NH.

12. The pharmaceutical composition according to claim 10, wherein A represents a hydrogen atom, a C₁-C₃-alkyl group or a hydroxymethyl group, B represents a hydrogen atom, a halogen atom, a cyano group or a nitro group, X represents a group of the formula

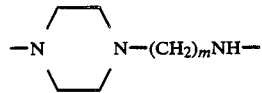

wherein m has the value 2, 3, 4, 5 or 6 and Y represents an oxygen atom or the group =NH.

13. The pharmaceutical composition according to claim 10, wherein A represents a hydrogen atom, a C₁-C₃-alkyl group or a hydroxymethyl group, B represents a hydrogen atom, a halogen atom, a cyano group or a nitro group, X represents a group of the formula

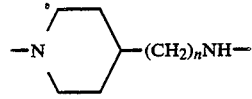

wherein n has the value 0, 1, 2, 3 or 4, and Y represents an oxygen atom or the group =NH.

14. The pharmaceutical composition according to claim 10, wherein A represents a hydrogen atom, a C₁-C₃-alkyl group or a hydroxymethyl group, B represents a hydrogen atom, a halogen atom, a cyano group or a nitro group, X represents a group of the formula —NH(CH₂)ₘNH— wherein m has the value 2, 3, 4, 5 or 6, and Y represents an oxygen atom or the group =NH.

15. The pharmaceutical composition according to claim 10, wherein A represents a hydrogen atom, a C₁-C₃-alkyl group or a hydroxymethyl group, a hydrogen atom, a halogen atom, a cyano group or a nitro group, X represents a group corresponding to one of the following formulae:

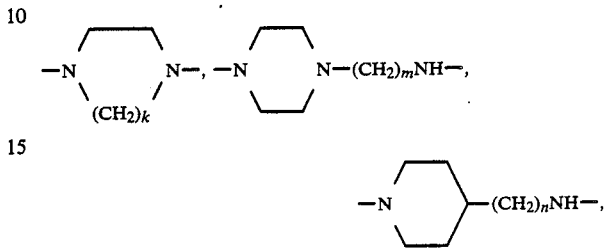

—NH—(CH₂)ₘNH—, —O(CH₂)ₙNH— or —(CH₂)ₙNH— wherein k has the value 1, 2 or 3, m has the value 2, 3, 4, 5 or 6 and n has the value 0, 1, 2, 3 or 4, and Y represents a group of the formula

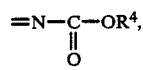

wherein R⁴ stands for a straight chain or branched C₁-C₄-alkyl group unsubstituted or substituted with one or more halogen atoms, C₁-C₃-alkoxy groups or phenyl groups.

16. A method for cardiotonically treating the heart in a mammalian organism, said method comprising administering a cardiotonically effective amount of a 6-oxopyridazine derivative corresponding to formula I:

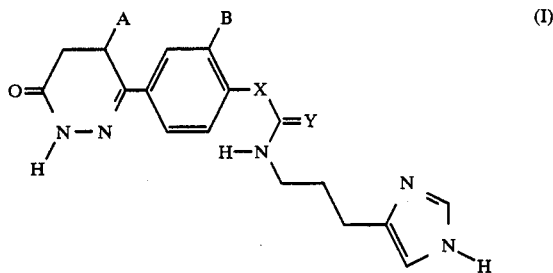

wherein A represents a hydrogen atom, a C₁-C₃-alkyl group or a hydroxymethyl group, B represents a hydrogen atom, a halogen atom, a cyano group or a nitro group, X represents a group corresponding to one of the following formulae:

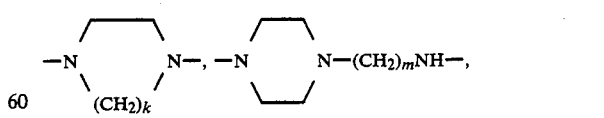

—NH(CH₂)ₘNH—, —O(CH₂)ₙNH— or —(CH₂)ₙNH— wherein k has the value 1, 2 or 3, m has the value 2, 3, 4, 5 or 6 and n has the value 0, 1, 2, 3 or 4, and Y represents an oxygen atom, a group corresponding to one of the following formulae =NH, =N—CN,

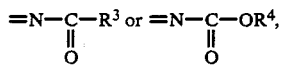

wherein R³ represents a straight chain or branched C₁-C₆-alkyl group or an aryl group which is unsubstituted or substituted with one or more halogen atoms, C₁-C₃-alkyl groups or C₁-C₃-alkoxy groups and R⁴ represents a straight chain or branched C₁-C₄-alkyl group unsubstituted or substituted with one or more halogen atoms, C₁-C₃-alkoxy groups or phenyl groups, or physiologically acceptable salt thereof to a mammalian organism in need of such treatment.

17. The method according to claim 16, wherein A represents a hydrogen atom, a C₁-C₃-alkyl group or a hydroxymethyl group, B represents a hydrogen atom, a halogen atom, a cyano group or a nitro group and X represents a group of the formula

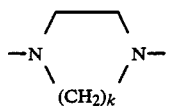

wherein k has the value 1, 2 or 3, and Y represents an oxygen atom or the group =NH.

18. The method according to claim 16, wherein A represents a hydrogen atom, a C₁-C₃-alkyl group or a hydroxymethyl group, B represents a hydrogen atom, a halogen atom, a cyano group or a nitro group, X represents a group of the formula

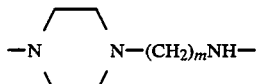

wherein m has the value 2, 3, 4, 5 or 6 and Y represents an oxygen atom or the group =NH.

19. The method according to claim 16, wherein A represents a hydrogen atom, a C₁-C₃-alkyl group or a hydroxymethyl group, B represents a hydrogen atom, a halogen atom, a cyano group or a nitro group, X represents a group of the formula

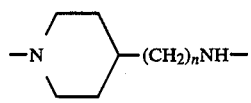

wherein n has the value 0, 1, 2, 3 or 4, and Y represents an oxygen atom or the group =NH.

20. The method according to claim 16, wherein A represents a hydrogen atom, a C₁-C₃-alkyl group or a hydroxymethyl group, B represents a hydrogen atom, a halogen atom, a cyano group or a nitro group, X represents a group of the formula —NH(CH₂)ₘNH— wherein m has the value 2, 3, 4, 5 or 6, and Y represents an oxygen atom or the group =NH.

21. The method according to claim 16, wherein A represents a hydrogen atom, a C₁-C₃-alkyl group or a hydroxymethyl group, B represents a hydrogen atom, a halogen atom, a cyano group or a nitro group, X represents a group corresponding to one of the following formulae:

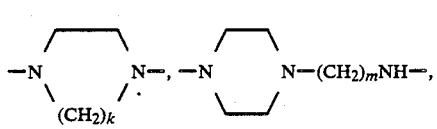

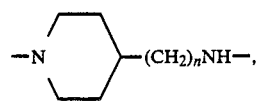

—NH—(CH₂)ₘNH—, —O(CH₂)ₙNH— or —(CH₂)ₙNH— wherein k has the value 1, 2 or 3, m has the value 2, 3, 4, 5 or 6 and n has the value 0, 1, 2, 3 or 4, and Y represents a group of the formula

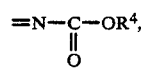

wherein R⁴ stands for a straight chain or branched C₁-C₄-alkyl group unsubstituted or substituted with one or more halogen atoms, C₁-C₃-alkoxy groups or phenyl groups.

22. A method for obtaining a positive inotropic action in the heart of a mammalian organism, said method comprising administering a positive inotropic effective amount of a 6-oxo-pyridazine corresponding to formula I:

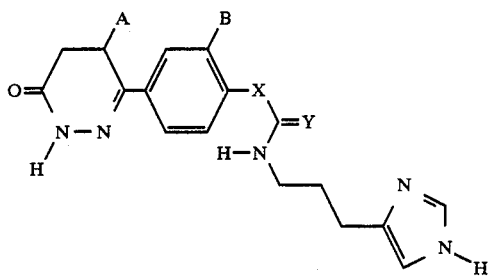

wherein A represents a hydrogen atom, a C₁-C₃-alkyl group or a hydroxymethyl group, B represents a hydrogen atom, a halogen atom, a cyano group or a nitro group, X represents a group corresponding to one of the following formulae:

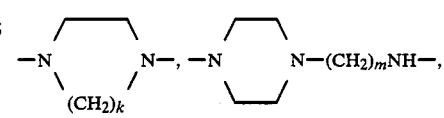

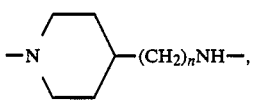

—NH(CH₂)ₘNH—, —O(CH₂)ₙNH— or —(CH₂)ₙNH— wherein k has the value 1, 2 or 3, m has the value 2, 3, 4, 5 or 6 and n has the value 0, 1, 2, 3 or 4, and Y represents an oxygen atom, a group corresponding to one of the following formulae =NH, =N—CN,

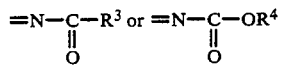

wherein $R^3$ represents a straight chain or branched $C_1$–$C_6$-alkyl group or an aryl group which is unsubstituted or substituted with one or more halogen atoms, $C_1$–$C_3$-alkyl groups or $C_1$–$C_3$-alkoxy groups and $R^4$ represents a straight chain or branched $C_1$–$C_4$-alkyl group unsubstituted or substituted with one or more halogen atoms, $C_1$–$C_3$-alkoxy groups or phenyl groups, or physiologically acceptable salt thereof, to a mammalian organism in need of such treatment.

* * * * *